US007117867B2

(12) United States Patent
Cox et al.

(10) Patent No.: US 7,117,867 B2
(45) Date of Patent: *Oct. 10, 2006

(54) AEROSOL GENERATOR AND METHODS OF MAKING AND USING AN AEROSOL GENERATOR

(75) Inventors: Kenneth A. Cox, Midlothian, VA (US); Timothy Paul Beane, Richmond, VA (US); William R. Sweeney, Richmond, VA (US); Walter A. Nichols, Chesterfield, VA (US); F. Murphy Sprinkel, Jr., Richmond, VA (US)

(73) Assignee: Philip Morris USA, Richmond, VA (US)

( * ) Notice: Subject to any disclaimer, the term of this patent is extended or adjusted under 35 U.S.C. 154(b) by 9 days.

This patent is subject to a terminal disclaimer.

(21) Appl. No.: 10/438,329

(22) Filed: May 15, 2003

(65) Prior Publication Data

US 2004/0050383 A1    Mar. 18, 2004

Related U.S. Application Data

(63) Continuation of application No. 10/247,776, filed on Sep. 20, 2002, now abandoned, which is a continuation of application No. 09/479,597, filed on Jan. 7, 2000, now Pat. No. 6,516,796, which is a continuation of application No. PCT/US99/24080, which is a continuation of application No. 09/172,023, filed on Oct. 14, 1998, now Pat. No. 6,234,167.

(51) Int. Cl.
*A61M 11/00*  (2006.01)
*A61M 15/00*  (2006.01)
*A61M 16/00*  (2006.01)
*F16K 11/00*  (2006.01)

(52) U.S. Cl. .................... 128/200.14; 128/200.18; 128/200.21; 128/203.12; 128/203.21; 128/203.25; 128/203.26

(58) Field of Classification Search ........... 128/200.14, 128/200.18, 200.21, 203.12, 203.21, 203.25, 128/203.26
See application file for complete search history.

(56) References Cited

U.S. PATENT DOCUMENTS

| | | |
|---|---|---|
| 2,896,856 A | 7/1959 | Kravits |
| 3,084,698 A | 4/1963 | Smith |
| 3,157,179 A | 11/1964 | Paullus et al. |
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 3,995,371 A | 12/1976 | O'Keefe |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,259,409 A | 3/1981 | Arnold |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |

| | | | | | | |
|---|---|---|---|---|---|---|
| 4,395,303 A | 7/1983 | Weir | | 5,556,964 A | 9/1996 | Hofstraat et al. |
| 4,433,797 A | 2/1984 | Galia | | 5,564,442 A | 10/1996 | MacDonald et al. |
| 4,471,892 A | 9/1984 | Coleman | | 5,565,677 A | 10/1996 | Wexler |
| 4,512,341 A | 4/1985 | Lester | | 5,575,929 A | 11/1996 | Yu et al. |
| 4,575,609 A | 3/1986 | Fassel et al. | | 5,585,045 A * | 12/1996 | Heinonen et al. .......... 261/72.1 |
| 4,627,432 A | 12/1986 | Newell et al. | | 5,617,844 A | 4/1997 | King |
| 4,649,911 A | 3/1987 | Knight et al. | | 5,642,728 A | 7/1997 | Andersson et al. |
| 4,682,010 A | 7/1987 | Drapeau et al. | | 5,674,860 A | 10/1997 | Carling et al. |
| 4,695,625 A | 9/1987 | Macdonald | | 5,682,874 A | 11/1997 | Grabenkort et al. |
| 4,700,657 A | 10/1987 | Butland | | 5,730,158 A | 3/1998 | Collins et al. |
| 4,730,111 A * | 3/1988 | Vestal et al. ................. 250/288 | | 5,743,251 A * | 4/1998 | Howell et al. ......... 128/200.14 |
| 4,735,217 A * | 4/1988 | Gerth et al. ................. 131/273 | | 5,755,218 A | 5/1998 | Johansson et al. |
| 4,744,932 A | 5/1988 | Browne | | 5,756,995 A | 5/1998 | Maswadeh et al. |
| 4,749,778 A | 6/1988 | Fukuzawa et al. | | 5,765,724 A | 6/1998 | Amberg et al. |
| 4,762,995 A | 8/1988 | Browner et al. | | 5,813,397 A | 9/1998 | Goodman et al. |
| 4,776,515 A * | 10/1988 | Michalchik .................... 239/3 | | 5,823,178 A | 10/1998 | Lloyd et al. |
| 4,790,305 A | 12/1988 | Zoltan et al. | | 5,839,430 A | 11/1998 | Cama |
| 4,811,731 A | 3/1989 | Newell et al. | | 5,855,202 A | 1/1999 | Andrade |
| 4,819,374 A | 4/1989 | Gemgnani | | 5,856,671 A | 1/1999 | Henion et al. |
| 4,819,834 A | 4/1989 | Thiel | | 5,863,652 A | 1/1999 | Matsumura et al. |
| 4,829,996 A | 5/1989 | Noakes et al. | | 5,869,133 A | 2/1999 | Anthony et al. |
| 4,837,260 A | 6/1989 | Sato et al. | | 5,872,010 A | 2/1999 | Karger et al. |
| 4,848,374 A | 7/1989 | Chard et al. | | 5,878,752 A | 3/1999 | Adams et al. |
| 4,871,115 A | 10/1989 | Hessey | | 5,881,714 A | 3/1999 | Yokoi et al. |
| 4,871,623 A | 10/1989 | Hoopman et al. | | 5,906,202 A | 5/1999 | Schuster et al. |
| 4,877,989 A * | 10/1989 | Drews et al. ......... 310/323.01 | | 5,914,122 A | 6/1999 | Otterbeck et al. |
| 4,911,157 A | 3/1990 | Miller | | 5,932,249 A | 8/1999 | Gruber et al. |
| 4,922,901 A | 5/1990 | Brooks et al. | | 5,932,315 A | 8/1999 | Lum et al. |
| 4,926,852 A | 5/1990 | Zoltan et al. | | 5,934,272 A | 8/1999 | Lloyd et al. |
| 4,935,624 A * | 6/1990 | Henion et al. .............. 250/288 | | 5,934,273 A | 8/1999 | Andersson et al. |
| 4,941,483 A | 7/1990 | Ridings et al. | | 5,944,025 A | 8/1999 | Cook et al. |
| 4,947,875 A | 8/1990 | Brooks et al. | | 5,954,979 A | 9/1999 | Counts et al. |
| 4,974,754 A | 12/1990 | Wirz | | 5,957,124 A | 9/1999 | Lloyd et al. |
| 4,982,097 A | 1/1991 | Slivon et al. | | 5,970,973 A | 10/1999 | Gonda et al. |
| 4,992,206 A | 2/1991 | Waldron | | 5,970,974 A | 10/1999 | Van Der Linden et al. |
| 5,021,802 A | 6/1991 | Allred | | 5,978,548 A | 11/1999 | Holmstrand et al. |
| 5,044,565 A | 9/1991 | Alexander | | 5,993,633 A | 11/1999 | Smith et al. |
| 5,056,511 A | 10/1991 | Ronge | | 6,014,970 A | 1/2000 | Ivri et al. |
| 5,060,671 A * | 10/1991 | Counts et al. ............... 131/329 | | 6,053,176 A | 4/2000 | Adams et al. |
| 5,063,921 A * | 11/1991 | Howe .................... 128/200.14 | | 6,054,032 A | 4/2000 | Haddad et al. |
| 5,096,092 A | 3/1992 | Devine | | 6,069,214 A | 5/2000 | McCormick et al. |
| 5,125,441 A | 6/1992 | Mette | | 6,069,219 A | 5/2000 | McCormick et al. |
| 5,133,343 A | 7/1992 | Johnson et al. | | 6,070,575 A | 6/2000 | Gonda et al. |
| 5,134,993 A * | 8/1992 | van der Linden et al. .................... 128/200.14 | | 6,071,428 A | 6/2000 | Franks et al. |
| | | | | 6,071,554 A | 6/2000 | Isomura et al. |
| 5,135,009 A | 8/1992 | Müller et al. | | 6,076,522 A | 6/2000 | Dwivedi et al. |
| 5,144,962 A | 9/1992 | Counts et al. | | 6,077,543 A | 6/2000 | Gordon et al. |
| 5,151,827 A | 9/1992 | Ven et al. | | 6,080,721 A | 6/2000 | Patton |
| 5,178,305 A | 1/1993 | Keller | | 6,085,740 A | 7/2000 | Ivri et al. |
| 5,184,776 A | 2/1993 | Minier | | 6,085,753 A | 7/2000 | Gonda et al. |
| 5,217,004 A * | 6/1993 | Blasnik et al. ......... 128/200.23 | | 6,089,228 A | 7/2000 | Smith et al. |
| 5,226,441 A | 7/1993 | Dunmire et al. | | 6,095,153 A | 8/2000 | Kessler et al. |
| 5,228,444 A * | 7/1993 | Burch ........................ 600/431 | | 6,098,615 A | 8/2000 | Lloyd et al. |
| 5,230,445 A | 7/1993 | Rusnak | | 6,098,620 A | 8/2000 | Lloyd et al. |
| 5,231,983 A | 8/1993 | Matson et al. | | 6,103,270 A | 8/2000 | Johnson et al. |
| 5,259,370 A * | 11/1993 | Howe .................... 128/200.14 | | 6,116,516 A | 9/2000 | Gañán-Calvo |
| 5,284,133 A * | 2/1994 | Burns et al. .......... 128/200.23 | | 6,116,893 A | 9/2000 | Peach |
| 5,290,540 A | 3/1994 | Prince et al. | | 6,119,953 A | 9/2000 | Gañán-Calvo |
| 5,298,744 A | 3/1994 | Mimura et al. | | 6,123,068 A | 9/2000 | Lloyd et al. |
| 5,299,565 A | 4/1994 | Brown | | 6,123,936 A | 9/2000 | Platz et al. |
| 5,322,057 A | 6/1994 | Raabe et al. | | 6,131,567 A | 10/2000 | Gonda et al. |
| 5,327,915 A | 7/1994 | Porenski et al. | | 6,131,570 A | 10/2000 | Schuster et al. |
| 5,342,180 A | 8/1994 | Daoud | | 6,136,346 A | 10/2000 | Eljamal et al. |
| 5,342,645 A | 8/1994 | Eisele et al. | | 6,138,668 A | 10/2000 | Patton et al. |
| 5,349,946 A * | 9/1994 | McComb ................ 128/203.17 | | 6,155,268 A | 12/2000 | Takeuchi |
| 5,395,445 A | 3/1995 | Bohanan | | 6,158,431 A | 12/2000 | Poole |
| 5,421,489 A | 6/1995 | Holzner, Sr. et al. | | 6,158,676 A | 12/2000 | Hughes |
| 5,462,597 A | 10/1995 | Jubran | | 6,159,188 A | 12/2000 | Laibovitz et al. |
| 5,474,059 A * | 12/1995 | Cooper ................. 128/200.22 | | 6,164,630 A | 12/2000 | Birdsell et al. |
| 5,487,378 A * | 1/1996 | Robertson et al. ..... 128/200.16 | | 6,165,463 A | 12/2000 | Platz et al. |
| 5,509,557 A | 4/1996 | Jimarez et al. | | 6,167,880 B1 | 1/2001 | Gonda et al. |
| 5,515,842 A | 5/1996 | Ramseyer et al. | | 6,174,469 B1 | 1/2001 | Gañán-Calvo |
| 5,522,385 A * | 6/1996 | Lloyd et al. ........... 128/203.26 | | 6,182,712 B1 | 2/2001 | Stout et al. |

| | | | |
|---|---|---|---|
| 6,187,214 B1 | 2/2001 | Gañán-Calvo | |
| 6,187,344 B1 | 2/2001 | Eljamal et al. | |
| 6,189,803 B1 | 2/2001 | Gañán-Calvo | |
| 6,192,882 B1 | 2/2001 | Gonda | |
| 6,197,835 B1 | 3/2001 | Gañán-Calvo | |
| 6,205,999 B1 * | 3/2001 | Ivri et al. | 128/200.22 |
| 6,206,242 B1 | 3/2001 | Amberg et al. | |
| 6,207,135 B1 | 3/2001 | Rössling et al. | |
| 6,223,746 B1 | 5/2001 | Jewett et al. | |
| 6,230,706 B1 * | 5/2001 | Gonda et al. | 128/203.12 |
| 6,231,851 B1 | 5/2001 | Platz et al. | |
| 6,234,167 B1 * | 5/2001 | Cox et al. | 128/200.14 |
| 6,234,402 B1 | 5/2001 | Gañán-Calvo | |
| 6,235,177 B1 | 5/2001 | Borland et al. | |
| 6,250,298 B1 | 6/2001 | Gonda et al. | |
| 6,257,233 B1 | 7/2001 | Burr et al. | |
| 6,258,341 B1 | 7/2001 | Foster et al. | |
| 6,263,872 B1 | 7/2001 | Schuster et al. | |
| 6,267,155 B1 | 7/2001 | Parks et al. | |
| 6,275,650 B1 | 8/2001 | Lambert | |
| 6,276,347 B1 | 8/2001 | Hunt | |
| 6,284,525 B1 | 9/2001 | Mathies et al. | |
| 6,288,360 B1 | 9/2001 | Beste | |
| 6,290,685 B1 | 9/2001 | Insley et al. | |
| 6,294,204 B1 | 9/2001 | Rössling et al. | |
| 6,295,986 B1 | 10/2001 | Patel et al. | |
| 6,318,361 B1 | 11/2001 | Sosiak | |
| 6,491,233 B1 * | 12/2002 | Nichols | 239/128 |
| 6,501,052 B1 * | 12/2002 | Cox et al. | 219/486 |
| 6,516,796 B1 * | 2/2003 | Cox et al. | 128/200.23 |
| 6,557,552 B1 * | 5/2003 | Cox et al. | 128/203.27 |
| 6,766,220 B1 * | 7/2004 | McRae et al. | 700/266 |
| 6,772,757 B1 * | 8/2004 | Sprinkel, Jr. | 128/203.26 |
| 6,923,179 B1 * | 8/2005 | Gupta et al. | 128/203.17 |
| 2001/0032647 A1 | 10/2001 | Schuster et al. | |

FOREIGN PATENT DOCUMENTS

| | | |
|---|---|---|
| BE | 354004 A | 9/1928 |
| BE | 354094 | 9/1928 |
| DE | 1036470 | 4/1958 |
| EP | 358114 | 3/1990 |
| EP | 642802 | 3/1995 |
| FR | 667979 | 10/1929 |
| HU | 168128 | 2/1976 |
| HU | 168128 | 4/1993 |
| HU | 207457 | 4/1993 |
| HU | P 95034-0 | 6/1994 |
| HU | 216121 | 4/1999 |
| WO | WO 94/09842 | 5/1994 |
| WO | WO 97/49441 A | 12/1997 |
| WO | 98/17131 | 4/1998 |
| WO | WO 98/17131 A | 4/1998 |

OTHER PUBLICATIONS

Supplementary Partial European Search Report for Appln. No. 999520003.4-2310/US9924080 dated Jun. 22, 2004.

Barry, P.W. et al., "In Vitro Comparison of the Amount of Salbutamol Availiable for Inhalation From Different Formulations Used with Different Spacer Devices" Eur Respir J 1997; 10: 1345-1348.

Hindle, Michael et al, "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97-102.

Hou, Shuguang et al. *Solution Stability of Budendonide in Novel Aerosol Formations* Abstract No. 2582, Solid State Physical Pharmacy, Nov. 17, 1998, p. S-307.

Morén, Folke "Drug Deposition of Pressurized Inhalation Aerosols I. Influence of Actuator Tube Design" AB Draco (Subsidiary of AB Astra, Sweden) Research and Development Laboratories Pack, S-221 01 Lund (Sweden), International Journal of Pharmaceutrics, 1 (1978) 205-212.

Newman, Stephen P. et al. "Deposition of Pressurized Suspension Aerosols Inhaled Through Extension Devices$_{1-3}$" Am Rev Respir Dis 1981; 124:317-320

Roth, G. et al. High Performance Liquid Chromatographic Determination of Epimers, Impurties, and Content of the Glucocorticoid Budesonide and Preparation of Primary Standard, Journal of Pharmaceutical Sciences, vol. 69, No. 7, pp. 766-770, Jul. 1980.

Kousaka et al., Generation of Aerosol Particles by Boiling of Suspensions, Aerosol Science & Technology, 1994, pp. 236-240.

Stimuli to the Revision process, Pharmocopeial Forum, May-Jun. 1994, pp. 7477-7505, vol. 20, No. 3.

European Communication Pursuant to Article 96(2) EPC dated Dec. 1, 2004 for Application No. 99 952 003.4-2310.

European Communication Pursuant to Article 96(2) EPC dated Sep. 15, 2005 for Application No. 99 952 003.4-2310.

* cited by examiner

*Primary Examiner*—Henry Bennett
*Assistant Examiner*—Nihir Patel
(74) *Attorney, Agent, or Firm*—Buchanan Ingersoll & Rooney PC

(57) ABSTRACT

An aerosol generator includes a flow passage having an inlet and an outlet, a heater arranged relative to the flow passage for heating the flow passage, a source of material to be volatilized in communication with the inlet of the flow passage, a valve to open and close communication between the source of material and the inlet of the flow passage, and a pressurization arrangement for causing material in the source of material to be introduced into the flow passage when the valve is in an open position. The aerosol generator further includes a source of power for operating the heater and the valve, and a control device for controlling supply of power from the source of power to the heater and the valve. A metering device in an inhaler includes a pressurized source of medicated fluid and a metering chamber configured to deliver a predetermined volume of fluid to a heated flow passage in the inhaler. The metering chamber can be part of a rotary valve having a bore and a displacement member moveable within the bore from a first position where the fluid is loaded into the bore to a second position where the predetermined volume is ejected out of the bore. Another metering chamber has an elastic portion of a delivery passage in fluid communication with the pressurized source of liquid and the elastic portion of the delivery passage is deformed to eject the predetermined volume.

11 Claims, 15 Drawing Sheets

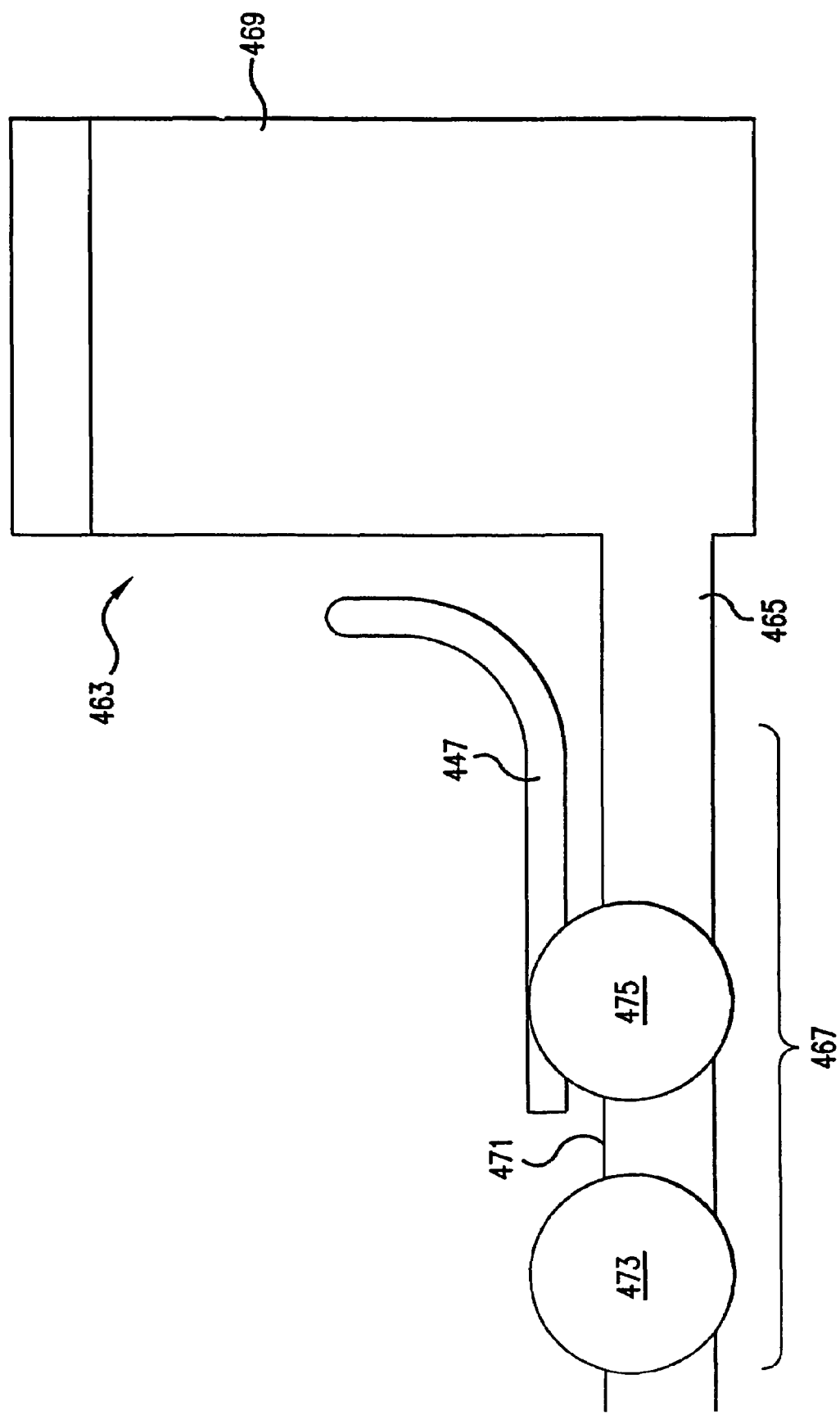

AEROSOL GENERATOR AND METHODS OF MAKING AND USING AN AEROSOL GENERATOR

This application is a continuation of application Ser. No. 10/247,776, filed on Sep. 20, 2002 ABN, which is a continuation of application Ser. No. 0/479,597, filed on Jan. 7, 2000 now U.S. Pat. No. 6,516,796, which is a continuation of PCT/US99/24080, filed Oct. 14, 1999, which is a continuation of application Ser. No. 09/172,023, filed Oct. 14, 1998 now U.S. Pat. No. 6,234,167.

BACKGROUND AND SUMMARY OF THE INVENTION

The present invention relates generally to aerosol generators and, more particularly, to aerosol generators able to generate aerosols without compressed gas propellants and methods of making and using such aerosol generators. The present invention also relates generally to metering valves in inhalers and, more particularly, to metering valves which deliver a predetermined volume in inhalers including aerosol generators able to generate aerosols without compressed gas propellants.

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, applying scents on the skin, and delivering paint and lubricant.

Various techniques are known for generating aerosols. For example, U.S. Pat. Nos. 4,811,731 and 4,627,432 both disclose devices for administering medicaments to patients in which a capsule is pierced by a pin to release a medicament in powder form. A user then inhales the released medicament through an opening in the device. While such devices may be acceptable for use in delivering medicaments in powder form, they are not suited to delivering medicaments in liquid form. The devices are also, of course, not well-suited to delivery of medicaments to persons who might have difficulty in generating a sufficient flow of air through the device to properly inhale the medicaments, such as asthma sufferers. The devices are also not suited for delivery of materials in applications other than medicament delivery.

Another well-known technique for generating an aerosol involves the use of a manually operated pump which draws liquid from a reservoir and forces it through a small nozzle opening to form a fine spray. A disadvantage of such aerosol generators, at least in medicament delivery applications, is the difficulty of properly synchronizing inhalation with pumping. More importantly, however, because such aerosol generators tend to produce particles of large size, their use as inhalers is compromised because large particles tend to not penetrate deep into the lungs.

One of the more popular techniques for generating an aerosol including liquid or powder particles involves the use of a compressed propellant, often containing a chlorofluoro-carbon (CFC) or methylchloroform, to entrain a material, usually by the Venturi principle. For example, inhalers containing compressed propellants such as compressed gas for entraining a medicament are often operated by depressing a button to release a short charge of the compressed propellant. The propellant entrains the medicament as the propellant flows over a reservoir of the medicament so that the propellant and the medicament can be inhaled by the user. Since the medicament is propelled by the propellant, such propellant-based arrangements are well-suited for those who might have difficulty inhaling. Nonetheless, aerosols generated by propellant-based arrangements have particles that are too large to ensure deep lung penetration.

In propellant-based arrangements, however, a medicament may not be properly delivered to the patient's lungs when it is necessary for the user to time the depression of an actuator such as a button with inhalation. Moreover, such arrangements tend to be poorly suited for delivery of materials in large quantities. Although propellant-based aerosol generators have wide application for uses such as antiperspirant and deodorant sprays and spray paint, their use is often limited because of the well-known adverse environmental effects of CFC's and methylchloroform, which are among the most popular propellants used in aerosol generators of this type.

In drug delivery applications, it is typically desirable to provide an aerosol having average mass median particle diameters of less than 2 microns to facilitate deep lung penetration. Most known aerosol generators are incapable of generating aerosols having average mass median particle diameters less than 2 to 4 microns. It is also desirable, in certain drug delivery applications, to deliver medicaments at high flow rates, e.g., above 1 milligram per second. Most known aerosol generators suited for drug delivery are incapable of delivering such high flow rates in the 0.2 to 2.0 micron size range.

U.S. Pat. No. 5,743,251, which is hereby incorporated by reference in its entirety, discloses an aerosol generator, along with certain principles of operation and materials used in an aerosol generator, as well as a method of producing an aerosol, and an aerosol. The aerosol generator disclosed according to the '251 patent is a significant improvement over earlier aerosol generators, such as those used as inhaler devices. It is desirable to produce an aerosol generator that is portable and easy to use.

According to one aspect of the present invention, an aerosol generator includes a flow passage such as a tube having an inlet and an outlet, a heater arranged relative to the flow passage for heating at least a portion of the flow passage, a source of material to be volatilized, the inlet of the flow passage being in communication with the source of material, and a valve operatively located between the source of material and the flow passage, the valve being openable and closeable to open and close communication between the source and the outlet of the flow passage. A pressurization arrangement is provided for causing material in the source of material to be introduced into the flow passage from the source of material when the valve is in an open position. A source of power is provided for operating the heater and for the valve, and a control device is provided for controlling supply of power from the source of power to the heater and the valve.

According to a further aspect of the present invention, a method of making an aerosol generator is disclosed. According to the method, a heater is arranged relative to a flow passage for heating of the flow passage, the flow passage having an inlet and an outlet. The inlet of the flow passage is connected to a source of material to be volatilized. An openable and closeable valve is provided between the source of material and the flow passage. A pressurization arrangement is provided for causing material in the source of material to be introduced into the flow passage from the source of material when the valve is in an open position. The valve is connected to a source of power for opening and closing the valve. The heater is connected to the source of power. The source of power is connected to a control device for controlling a supply of power from the source of power to the heater and the valve.

According to yet another aspect of the present invention, a method of generating an aerosol is disclosed. According to the method, a first signal indicative of a user's intention to generate an aerosol, is generated and sent to a control device. With the control device and responsive to the first signal, a second signal is sent to a source of power to cause the source of power to open an openable and closeable valve, the valve being disposed between a source of material to be volatilized and a flow passage, opening of the valve permitting material from the source of material to flow from the source of material and into the flow passage. Material from the source of material is thus caused to flow from the source of material and into the flow passage. With the control device and responsive to the first signal, a third signal is sent to the source of power to supply power to a heater disposed relative to the flow passage to heat the flow passage. Material from the source of material is heated in the flow passage with the heater to a vaporization temperature such that the material volatilizes and expands out of an outlet of the flow passage.

The present invention also provides a metering device in an inhaler having a pressurized source of medicated fluid and a metering chamber in fluid communication with the pressurized source of fluid. The metering chamber is configured to deliver a predetermined volume of fluid to a heated flow passage in an inhaler.

In accordance with one embodiment of the metering device, the metering chamber is a rotary valve including a bore and a displacement member located within the bore. The displacement member is movable from a first position where the fluid is loaded into a load portion of the bore to a second position where the predetermined volume of fluid is ejected out of the bore.

In accordance with another embodiment of the metering device, the metering device includes a delivery passage including an elastic portion. The metering chamber is located in the elastic portion of the delivery passage. The elastic portion of the delivery passage is compressed to eject a predetermined volume of liquid.

In accordance with another aspect of the invention, the inhaler preferably includes an aerosol generator wherein a flow passage has an inlet and an outlet and a pressurized source of fluid, a heater is arranged relative to the flow passage for heating at least a portion of the flow passage; and a metering chamber is in fluid communication with the pressurized source of fluid and is configured to deliver a predetermined volume to the flow passage.

In accordance with another aspect of the invention, a method of dispensing a predetermined volume of medicated fluid in an inhaler is provided wherein the inhaler includes a metering device having a pressurized source of fluid which is in fluid communication with a metering chamber. According to the method, the metering chamber is filled with fluid from the pressurized source and a predetermined volume of the fluid is ejected from the metering chamber into a heated flow passage.

BRIEF DESCRIPTION OF THE DRAWINGS

The features and advantages of the present invention are well understood by reading the following detailed description in conjunction with the drawings in which like numerals indicate similar elements and in which:

FIGS. 11A–11C are schematic cut-away views of another metering device according to the present invention;

DETAILED DESCRIPTION

Figure 1:
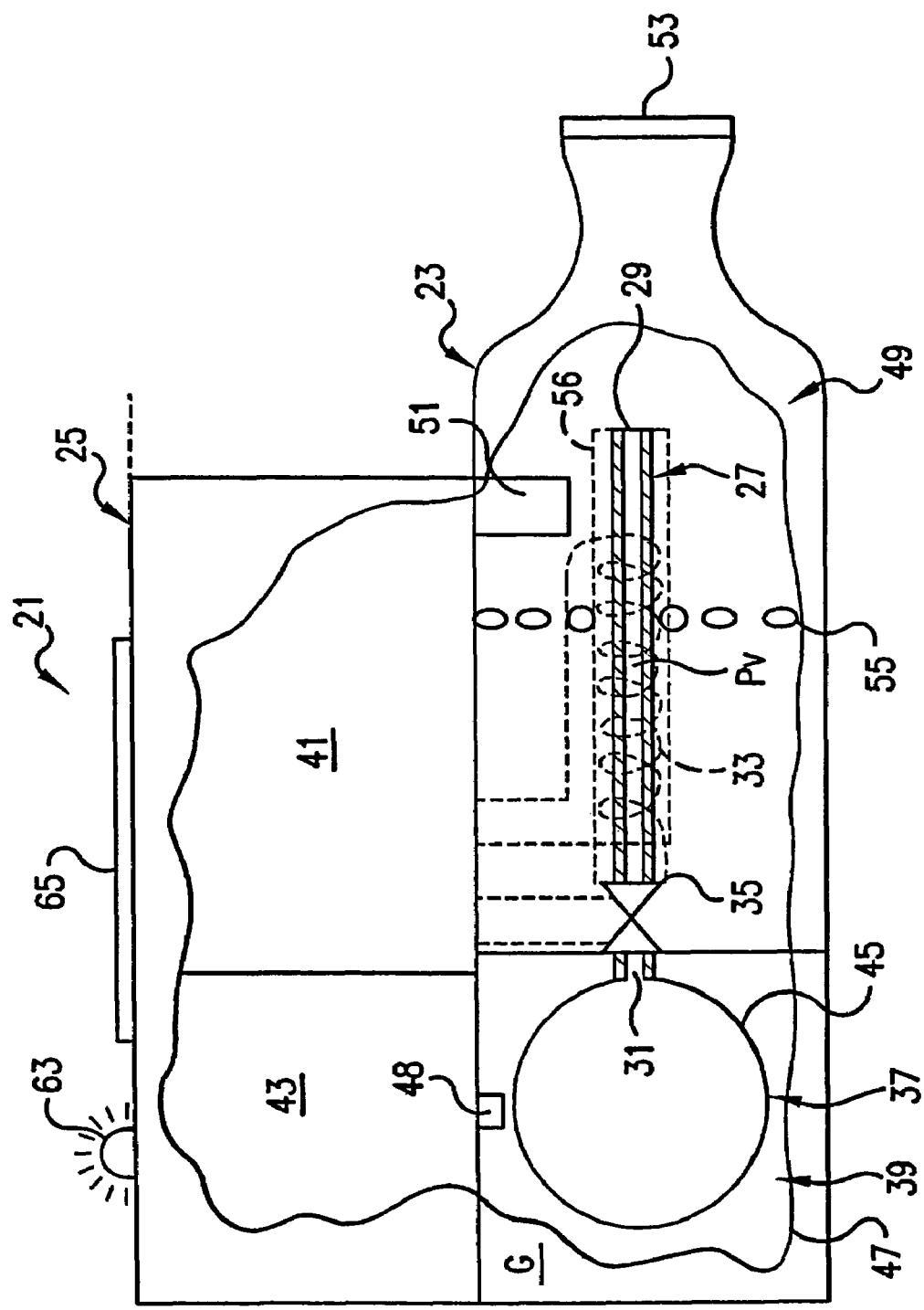
FIG. 1 is a schematic, partially broken, side view of an aerosol generator according to an embodiment of the present invention.

An aerosol generator 21 according to the present invention is shown in FIG. 1. The principles of operation of the aerosol generator 21 and, where applicable, materials used in the aerosol generator are preferably similar to the principles of operation and materials used in the aerosol generator disclosed in U.S. Pat. No. 5,743,251, which is hereby incorporated by reference in its entirety.

A preferred application for the aerosol generator 21 is as an inhaler device, such as an inhaler for medicaments, such as asthma medication and pain killers or any other therapeutic agents for treatment of a bodily condition. The aerosol generator 21 preferably includes a first component 23, which preferably includes, for example, the material to be turned into an aerosol and which is preferably disposable after one or a predetermined plurality of uses, removably attached to a second component 25, which preferably includes, for example, power source and logic circuitry structures and which is preferably permanent in the sense that it is reusable with successive ones of the first components. The first and second components 23 and 25 can be, attachable to one another in end to end or side by side relationships. If desired or necessary, however, the aerosol generator can be a one-piece device.

The first component 23 preferably includes a flow passage in the form of a tube 27 having a first and a second end 29, 31, and a heater 33 arranged relative to the tube for heating the tube. A valve 35 is provided either on the tube 27 or between the second end 31 of the tube and a source 37 of material, the valve preferably being openable and closeable to open and close communication between the first end 29 of the tube and the source of material. The valve 35 may define the second end 31 of the tube. The valve 35 is preferably electronically openable and closeable, preferably a solenoid-type valve. The first component 23 preferably further includes the source 37 of material to be volatilized. The first component 23 preferably also includes a pressurization arrangement 39 for causing material in the source 37 of material to be introduced into the tube 27 from the source of material when the valve 35 is in an open position.

The second component 25 is preferably attachable and detachable to the first component 23 and includes a source 41 of power for the heater 33 and for the valve 35, and a control device 43, such as a microchip, for controlling supply of power from the source of power to the heater and the valve. The source 41 of power is preferably a battery, more preferably a rechargeable battery, however, the source of power may, if desired or necessary, be a non-depleting source of power, such as a conventional power line. International Publication No. WO 98/17131 discloses a power controller and a method of operating an electrical smoking system that discloses a power source and a control device, particularly for heaters, the principles of operation and features of which are transferrable to the present invention, and is hereby incorporated by reference.

In WO 98/17131 power is applied to a heater element in accordance with a predetermined series of phases with each phase assigned different target total energies per phase and predetermined time periods for each phase such that a heat treatment event is achieved. In WO 98/17131 the controller is configured to modulate power in each phase so that the target energies are maintained irrespective of externalities such as battery voltage or the like. Preferably all liquid entering the flow passage formed by the tube 27 is volatilized before being discharged from the tube 27. Power modulation within one or more phases of a power cycle as described above can optionally be used to assure that such volatilization occurs consistently over a broad range of battery voltages such as those encountered along a battery discharge cycle.

General operation of the aerosol generator 21 involves a user providing a signal, such as by compressing a button or performing some other action such as inhaling near the first end 29 of the tube 27 to actuate a flow sensing detector or a pressure drop sensing detector, which is received by the control device 43. In response to the signal, the control device 43 preferably controls the supply of power from the power source 41 such that the valve 35 is opened and power is supplied to the heater 33 to cause it to heat up to its desired operating temperature. It may be desired or necessary, depending upon the application and the equipment employed, to open the valve 35 before or after supplying power to the heater 33.

Upon opening the valve 35, the pressurization arrangement 39 causes material in the source 37 of material to be introduced into the tube 27. The material in the tube 27 is heated to a vaporization temperature in the tube, volatilizes, and expands out of the free first end 29 of the tube. Upon exiting the tube 27, the volatilized material contacts cooler air and condenses to form an aerosol. Preferably, after a predetermined period of time, the control device 43 automatically closes the valve 35 and shuts off the supply of power to the heater 33. After one or a plurality of uses, the first component 23 is preferably separated from the second component 25 and is disposed of, and a new first component is attached to the second component for further use.

Because presently preferred applications for the aerosol generator 21 include use as an inhaler, the aerosol generator is preferably as small as possible. The valve 35 is preferably a microvalve. More preferably, the valve 35, the heater 33, and the tube 27 are a single microelectronic machine formed on a single chip. To the extent that other components of the aerosol generator 21 disclosed in the present application are subject to production as microelectronic devices, they may also be formed on a single chip with the valve 35, the heater 33, and the tube 27, or on another chip.

According to the preferred embodiment, the source 37 of material includes a flexible container 45, and the pressurization arrangement 39 includes a chamber 47 in which the flexible container is disposed. A pressurized gas G is preferably sealed in the chamber 47 and surrounds the flexible container 45. The pressurization arrangement 39 is preferably a so-called sepra container of the type used for dispensing, for example, gel shaving creams, caulking compounds, and depilatories, although other pressurization arrangements for delivering the material, such as propellants and manual or automatic pumps, may be used if desired or necessary. The sepra container pressurization system is particularly preferred, however, particularly due to its capacity for resistance to surrounding temperature variations, as well as to variations in pressure of the gas G because the gas is not depleted. When it is desired to dispense material from the source 37 of material, and the valve 35 is opened, the pressure of the gas G, which is preferably about two atmospheres (about 30 psi) greater than ambient pressure, compresses the flexible container 45, causing material to enter the tube 27 through the second end 31 of the tube in communication with the source of material. A preferred gas G is nitrogen because of its ready availability and comparatively low cost, although various other gases are also suitable and may be preferred for particular applications.

Displacement of material from the flexible container 45 means that there is more room in the chamber 47, which means that the gas G enclosed in the chamber occupies a greater volume. Preferably, the size of the flexible container 45 relative to the size of the chamber 47 is selected such that pressure of the gas G is about ten percent lower when the flexible container is empty than when the flexible container is full.

Figure 2:
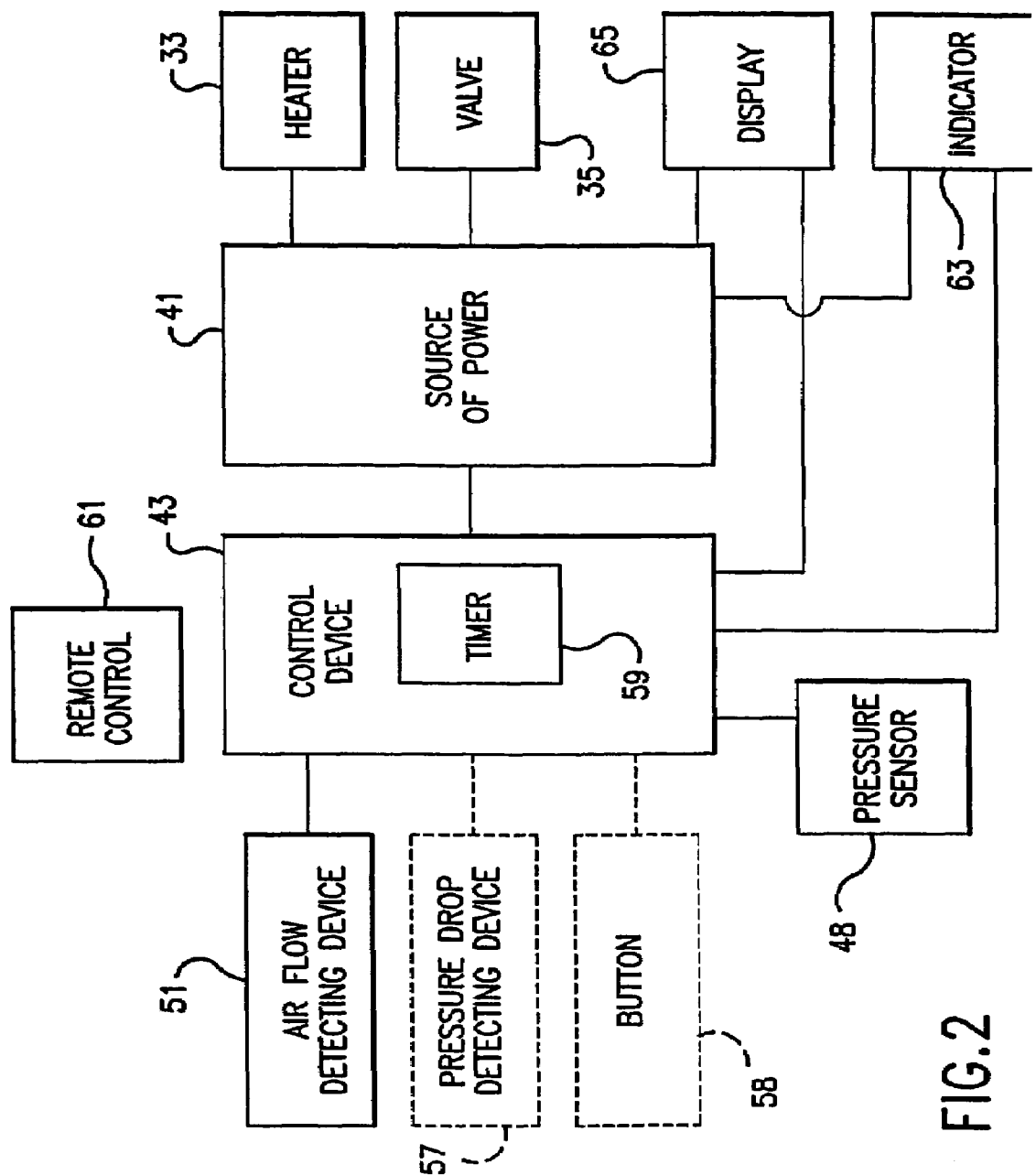
FIG. 2 is a logic diagram of powered components of an aerosol generator according to an embodiment of the present invention.

A pressure sensor 48 may be provided to sense the pressure of the gas G in the chamber 47. As seen in FIG. 2, the pressure sensor 48 is preferably arranged to send a signal representative of the pressure in the chamber 47 to the control device 43. The control device 43, in turn, is preferably arranged to control the power source 41 to adjust a length of time that power is supplied to the valve 35, and if desired or necessary, to the heater 33, in response to the signal from the pressure sensor. In this way, pressure drops in the chamber 47, which may result in a decrease in the rate at which material in the flexible container 45 is dispensed, can be compensated for by dispensing material for somewhat longer periods of time, i.e., by keeping the valve 35 open longer and, if desired or necessary, maintaining a supply of power to the heater 33.

A signal to the control device 43 to supply power to the valve 35 and the heater 33 and, where provided, other features of the aerosol generator 21, is preferably provided by a user of the aerosol generator. While the signal may be provided by, for example, pressing a button, turning a knob, or switching a switch, a preferred arrangement for providing a signal is based on a user causing some manner of air flow in the proximity of the free first end 29 of the tube 27, such as by inhaling on a mouthpiece section 49 of the aerosol generator. The aerosol generator 21 preferably includes an air flow detecting device 51 for determining when a predetermined air flow rate exists proximate the first end 29 of the tube 27. The air flow detecting device 51 is preferably arranged to send a signal to the control device 43 to indicate that the predetermined air flow rate exists, which may be indicative that a user is drawing on the open end 53 of the mouthpiece 49 section, and the controller is preferably arranged to control the power source to supply power to the valve 35 and the heater 33, and any other components, in response to the signal from the air flow detecting device. As seen in FIG. 1, the air flow detecting device 51 is preferably disposed transversely to and upstream of the first end 29 of the tube 27 so that the air flow detecting device will assist in ensuring that an adequate supply of air flow exists to produce and effectively deliver an aerosol from the volatilized material as it expands out of the first end of the tube.

Where the aerosol generator 21 is a multi-piece device, the air flow detecting device 51 is preferably permanently attached to the second component 25 and is, thus, preferably a permanent component, i.e., it is not disposed of. If desired or necessary, however, the air flow detecting device 51 can be a disposable component forming part of the first component 23 and can be removably connected, such as through an electrical connection, to the control device 43.

The mouthpiece section 49 preferably has an open end 53. The tube 27 is preferably disposed in the mouthpiece section 49 and the first end 29 of the tube is preferably disposed inside of the mouthpiece section at a distance from the open end 53 to permit complete mixing of volatilized material expanding out of the first end of the tube with surrounding air to form an aerosol. To ensure an adequate supply of air for mixing with the volatilized material, as well as to ensure an adequate supply of air for permitting a user to draw on the mouthpiece section and actuate the air flow detecting device 51, the mouthpiece section 49 preferably has a plurality of vent holes 55. To facilitate the flow of air past the first end 29 of the tube 27 and thereby facilitate formation of an aerosol, the first end of the tube is preferably disposed in the mouthpiece section 49 between the vent holes 55 and the open end 53 of the mouthpiece section. The vent holes 55 are preferably located relative to the tube 27, preferably close to the end 29, such that air passing through the vent holes has no or minimal cooling effect on the tube. The tube 27 may, of course, be insulated from air flowing through the vent holes 55, such as by providing insulation material or a concentric tube 56 (shown in phantom) or the like around the tube to channel air away from the tube.

As an alternative to, or in addition to, using an air flow detecting device 51 to send a signal to the control device 43, as seen in FIG. 2 in phantom, a pressure drop detecting device 57 for determining when a predetermined pressure drop occurs proximate the first end 29 of the tube 27 may be used. The pressure drop detecting device 57 is preferably arranged to send a signal to the control device 43 to indicate that the predetermined pressure drop is occurring, which may be indicative of a user drawing on the open end 53 of the mouthpiece section 49, and the control device is arranged to control the power source 41 to supply power to the valve 35 and the heater 33, and any other electrically powered components, in response to the signal from the pressure drop detecting device.

A suitable pressure drop detecting device is a puff-actuated sensor in the form of a Model 163PC01D35 silicon sensor, manufactured by MicroSwitch division of Honeywell, Inc., Freeport, Ill., or an SLP004D 0–4" $H_2O$ Basic Sensor Element, manufactured by SenSym, Inc., Milpitas, Calif. Other known flow-sensing devices, such as those using hot-wire anemometry principles, are also believed to be suited for use with the aerosol generator 21. The use of an air flow detecting device 51, as compared to a pressure drop detecting device, is presently preferred for inhaler-type applications because it is anticipated that an air flow detecting device will be easier for users to actuate as compared to a pressure drop detecting device.

Presently anticipated applications for the aerosol generating device 21 include drug delivery applications. For such applications, as well as in other applications to which the aerosol generating device 21 might be applied, the control device 43 may include a timer 59 for controlling a frequency with which the control device controls the power supply 41 to supply power to the valve 35 and the heater 33 and other components. In this way, the aerosol generating device 21 can automatically limit the frequency with which a user can operate the aerosol generating device, thereby facilitating in preventing accidental misuse and overdosages. Moreover, to assist caregivers in treating their patients, the aerosol generator 21 can be associated with a remote control device 61 remote from the control device 43. The remote control device 61 is preferably capable of adjusting the timer 59 to adjust the frequency with which the control device 43 controls the power supply 41 to supply power to the valve 35 and the heater 33, and other components. In this way, when a caregiver desires to increase or decrease the frequency with which the user is able to operate the aerosol generator, the caregiver can do so in situations where the caregiver and the user are separated by some distance. In this way, users who might otherwise be required to personally see their caregivers to have their treatment schedules adjusted have greater mobility.

The control device 43 and, if provided, the remote control device 61, may also be configured to permit adjustment or remote adjustment of other powered components of the aerosol generator 21, such as the length of time that the valve 35 is open, and the length of time that power is supplied to the heater from the power source 41. In this manner, it is possible to adjust dosages up or down, as well as to adjust operating conditions of the aerosol generator 21 to maintain the same operation where, for example, pressure of the gas G in the chamber 47 drops or the rate at which power is supplied from the power source 41 reduces, such as where the aerosol generator is used in different temperatures, material in the flexible container 45 is used up, or the charge of a battery forming the power source diminishes.

The timer 59 of the control device preferably is associated with an indicator 63, such as a beeper or light forming part of the timer or, for example, electrically connected to the timer, for indicating that the control device 43 is available to control the power supply 41 to supply power to the valve 35 and the heater 33 and other components. Where, for example, the aerosol generator 21 is used to dispense medication, the indicator 63 serves to remind the user that it is time for the medication. The indicator 63 may also, if desired or necessary, be operable by the remote control device 61. The indicator 63 may also be used to indicate to a user a length of time since the aerosol generator 21 was actuated, such as where the aerosol generator is used as an inhaler, and the user is supposed to hold his or her breath for a length of time after inhaling, with the indicator 63 indicating when a period of time has elapsed.

The aerosol generator 21 may also include a display device 65, such as an LCD display, for displaying information such as a number of times that the control device 43 controls the power supply 41 to supply power to the valve and the heater. The display device 65 may display, for example, a number of times that the aerosol generator 21 has been operated, e.g., 1 or 2 or 3, or a number of operations remaining, which may be based on, for example, the size of the source 37 of material and the amount of material dispensed each time that the valve 35 is opened and closed, or the life of the power supply 41, such as the remaining life of a battery. The same or additional display devices can be provided to display other information, such as pressure in the pressure chamber 47 and power level of the power source 41. Further, the aerosol generator 21 may be equipped with various sensors and displays to provide feedback to be displayed in a display device 65 to, for example, assist a user in learning how to use the aerosol generator properly as an inhaler, such as sensors to measure the volume and duration of an inhalation after completion of an inhalation, and even to provide feedback during an inhalation to assist the user in employing an optimum inhalation profile. The display device 65 is preferably controlled by the control device 43 and powered by the power supply 41.

The control device 43 may be individually programmable, such as by a pharmacist, to control the aerosol generator 21 to dispense medications according to a prescription, i.e., quantity of medication, frequency, etc., as well as programming in the information that would prevent improper use of the aerosol generator. In this manner, fewer types of aerosol generators 21 may be useful for a wide range of medications. The particular aerosol generator 21 would preferably be optimized for different classes of medications and then "fine tuned" by, for example, the pharmacist, for a specific drug or prescription.

The aerosol generator 21 may also be programmed to permanently prevent use after a set period of time. In this way, it would be possible to prevent the use of expired medications. This may be accomplished by, for example, having a battery power source 41 be non-replaceable, or by incorporating a battery and/or control device that keeps track of date and time and prevents operation past a particular date and time.

While not wishing to be bound by theory, depending upon selection of factors presently understood to primarily include a rate of power supplied from the source of power 41 to the heater 33, a diameter of the tube 27, and the material to be volatilized and delivered as an aerosol, the aerosol generator 21 is preferably specifically designed to generate an aerosol having certain desired characteristics. For many applications, particularly for medication delivery applications, the aerosol generator 21 according to the present invention is preferably designed to produce an aerosol having a mass median particle diameter of less than 3 microns, more preferably less than 2 microns, still more preferably between 0.2 and 2 microns, and still more preferably between 0.5 and 1 microns. While not wishing to be bound by theory, depending upon selection of factors presently understood to primarily include a length of the tube 27, a pressure with which the pressurization arrangement 39 supplies the material from the source 37 of material, and a rate at which power is supplied from the source 41 of power, the rate at which the material is supplied and volatilized in the tube is established. The aerosol generator 21 is preferably designed to supply and volatilize material at a rate greater than 1 milligram per second.

Figure 3:
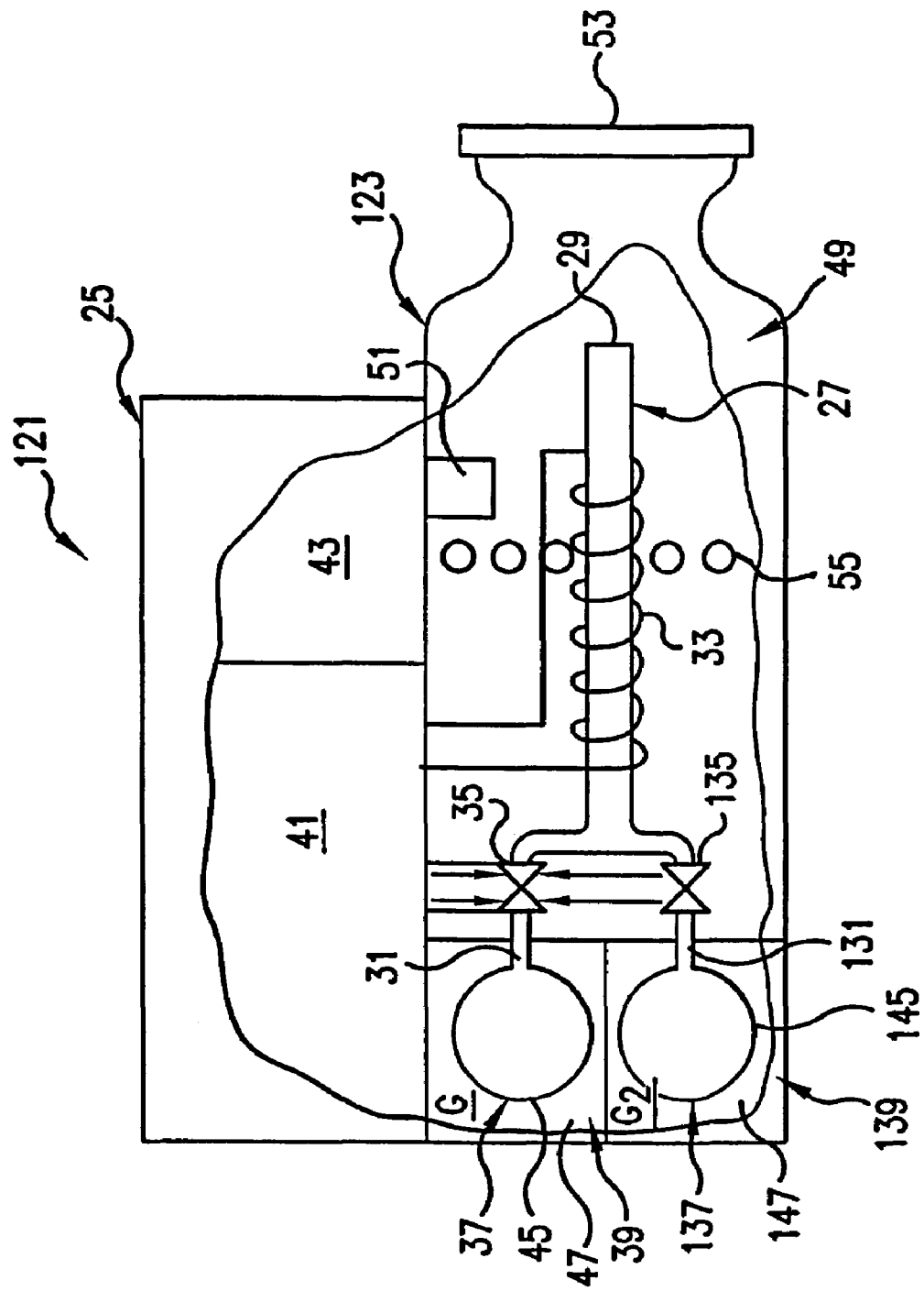
FIG. 3 is a schematic, partially broken, side view of an aerosol generator according to a second embodiment of the present invention.

It may be desirable to produce an aerosol formed from different liquid components that, for a variety of reasons, may be best kept separated until the moment that it is desired to form the aerosol. As seen in FIG. 3, another embodiment of the aerosol generator 121 may, in addition to the features described with respect to the aerosol generator 21, include, preferably as part of a modified first component 123, a source 137 of a second material in liquid form that is supplied to the tube 27 together with the material from the first source of material 37. The source 137 of second material preferably communicates with the tube 27 at a point 171 before the heater 33. A separate valve 135 is preferably powered by the power source 41 and controlled by the control device 43 to permit the pressurization arrangement 39 to cause material in the source 137 of second material to be introduced into tube 27 from the source of second material when the valve 35 is in an open position. If desired or necessary, the valve 35 and the valve 135 can be opened and closed at different times.

The source 137 of second material preferably includes a second flexible container 145. The pressurization arrangement 39 preferably includes a second chamber 147 in which the second flexible container 145 is disposed, and a second pressurized gas $G_2$ sealed in the second chamber and surrounding the second flexible container. The pressurized gas G and the second pressurized gas $G_2$ may be pressurized to different pressures to facilitate delivery of the material and the second material to the tube 27 at different rates. If desired or necessary, the flexible container 45 and the second flexible container 145 may be disposed in the same pressurized chamber. Additional sources of material and other components may be provided to produce an aerosol having still further components.

Figure 4:
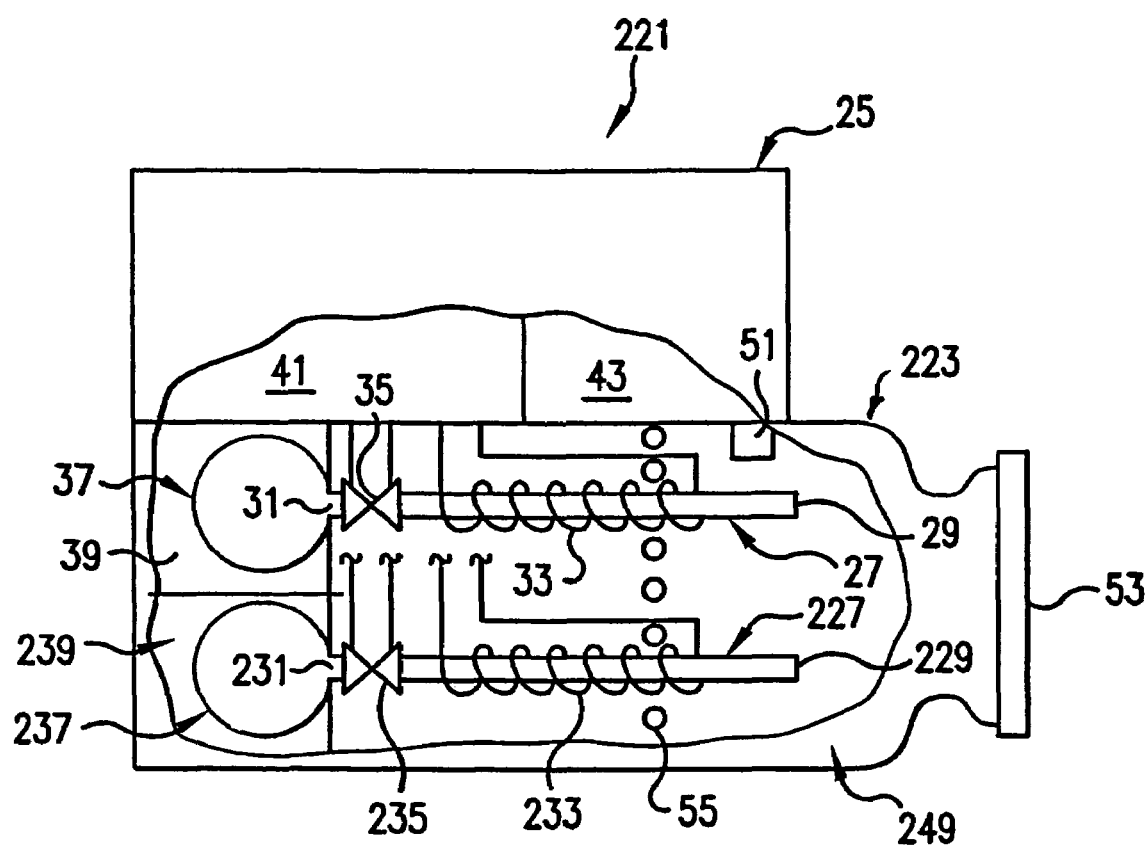
FIG. 4 is a schematic, partially broken, side view of an aerosol generator according to a third embodiment of the present invention.

As seen with respect to FIG. 4, a third embodiment of the aerosol generator 221 may include, preferably as part of a modified first component 223, a structure, or several structures, that is substantially entirely parallel to the structure of the first component to permit generation of an aerosol formed from two or more components. The aerosol generator 221 preferably includes a second tube 227 having a first and a second end 229, 231. A second heater 233 is preferably arranged relative to the second tube 227 for heating the second tube. A second valve 235 is preferably provided on the second tube 227 and is openable and closeable to open and close communication between the first and the second ends 229 and 231 of the second tube. A source 237 of second material to be volatilized is provided and the second end 231 of the second tube 227 communicates with the source of second material. A second pressurization arrangement 239 is provided for causing material in the source 237 of second material to be introduced into the second tube 227 from the source of second material when the second valve 235 is in an open position. If desired or necessary, the pressurization arrangement 39 can be used to cause material in the source 237 of second material to be introduced into the second tube 227. Preferably, the source 41 of power supplies power for the second heater 233 and for the second valve 235, as well as to any other electrically powered components of the aerosol generator, and the control device 43 controls supply of power from the source of power to the second heater and the second valve.

The aerosol generator 221 preferably includes a chamber 249, such as a mouthpiece section. The first ends 29 and 229 of the tube 27 and the second tube 227 are preferably disposed in the chamber 249 proximate each other. The chamber 249 is preferably of sufficient size and configuration to permit mixture of volatilized material and volatilized second material that expands out of the tube 27 and the second tube 227 together with ambient air such that the volatilized material and the volatilized second material form first and second aerosols, respectively, the first and second aerosols being mixed with each other to form a combination aerosol including the first and second aerosols.

In the embodiment described with reference to FIG. 1, a combination aerosol can be formed by providing material in the source 37 of material that includes two or more components mixed together before the material is volatilized. While the components in the source 37 of material may be two or more liquids, it is also possible to suspend solid particles in solution in a liquid material, or to dissolve solid particles in a liquid material. If desired or necessary, the solid particles, when suspended in solution, may be of a larger average diameter than particles of the material in aerosol form. The solid particles, when they form a part of the aerosol, may be of a larger average diameter than particles of the material in aerosol form. Solid particles can, of course, also be suspended in solution in liquid materials in the embodiments described with reference to FIGS. 3 and 4.

Figure 5:
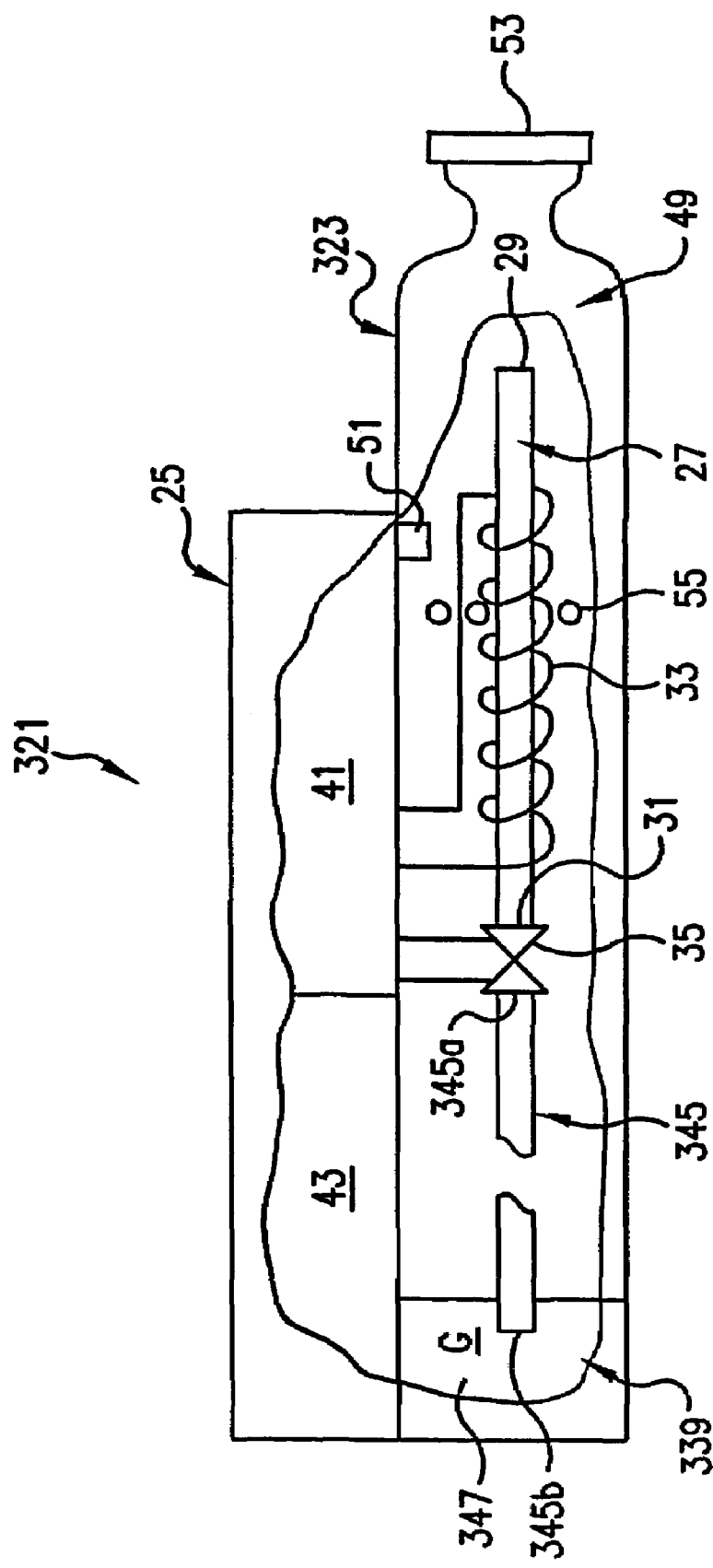
FIG. 5 is a schematic, partially broken, side view of an aerosol generator according to a fourth embodiment of the present invention.

As noted, a preferred pressurization arrangement 39 for the aerosol generator 21 includes a sepra container type of arrangement. An aerosol generator 321 having an alternative pressurization arrangement 339 is shown in FIG. 5. In this embodiment, the source 337 of material preferably includes a second tube 345 having first and second ends 345a, 345b. The first end 345a of the second tube 345 is connected to the second end 31 of the tube 27. The pressurization arrangement 339 includes a chamber 347 filled with a pressurized gas G. The second end 345b of the second tube 345 is disposed in the chamber 347 and is open to the chamber. The source 337 of material, the second tube 345, and the tube 27 preferably form part of a modified first component 323.

Figure 6A:
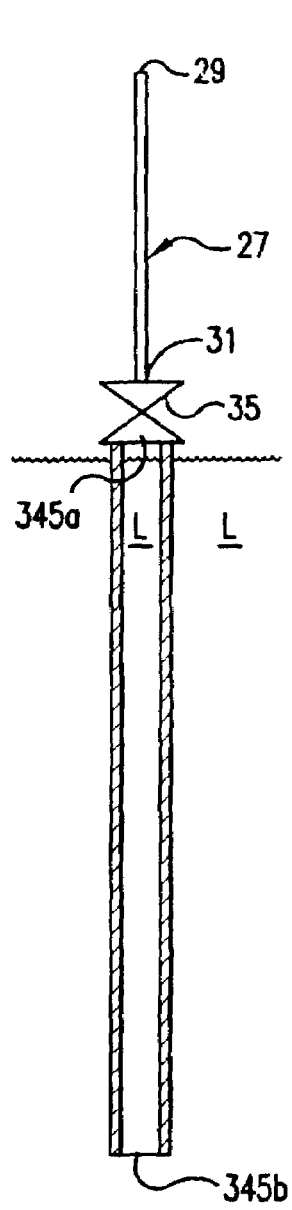
FIGS. 6A–6C show steps according to a method, according to a further aspect of the present invention, of manufacturing an aerosol generator according to the fifth embodiment of the present invention.
Figure 6B:
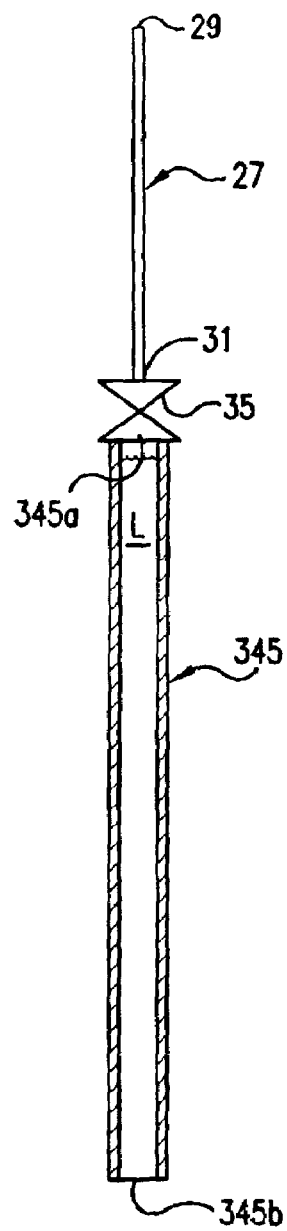
Figure 6C:
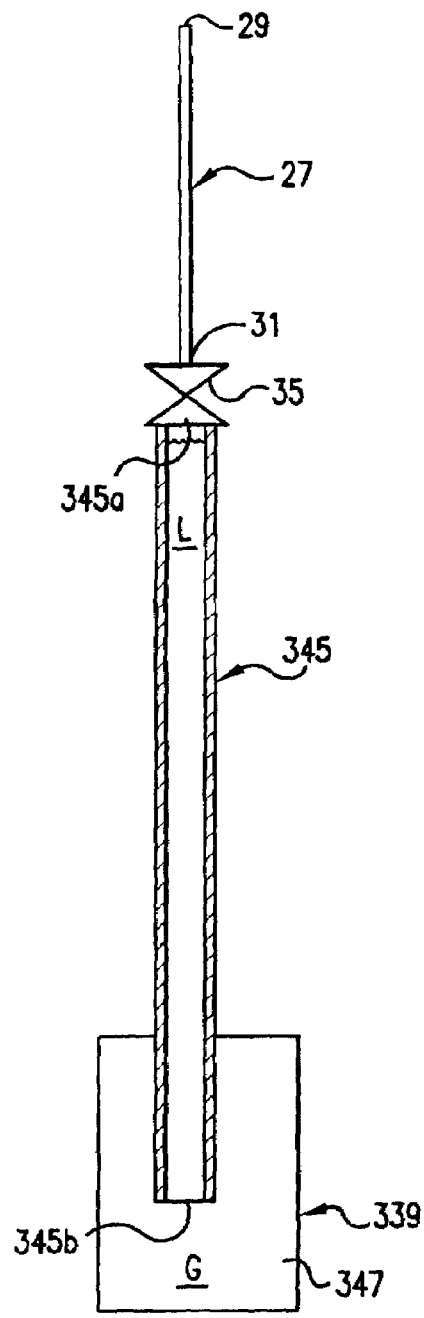

As seen in FIGS. 6A–6C, the source 337 of material is preferably filled with material by first opening the valve 35 in the tube 27, then immersing the open second end 345b of the second tube 345 in liquid material L (FIG. 6A). After the liquid material in which the second tube 345 is immersed fills the second tube, the valve 35 is then shut. The second tube 345 is withdrawn from the liquid material, with the liquid material that filled the second tube remaining in the second tube due to closure of the valve (FIG. 6B), i.e., air is unable to get behind the liquid material in the second tube. The second tube 345 is then positioned in the chamber 347 and the chamber is pressurized (FIG. 6C). When the valve 35 is opened, the pressure in the chamber forces the liquid material in the second tube 345 to enter the tube 27 where it can be volatilized by the heater 27.

In a method of making the aerosol generator 21 described with reference to the embodiment shown in FIG. 1, the heater 33 is arranged relative to the tube 27 to permit heating of the tube. The second end 31 of the tube 27 is connected to the source 37 of material to be volatilized. The openable and closeable valve 35 is provided to allow and stop communication between the source 37 of material and the tube 27.

The pressurization arrangement 39 for causing material in the source 37 of material to be introduced into the tube 27 from the source of material when the valve 35 is in an open position is provided. The valve 35 is connected to the source 41 of power for opening and closing the valve. The heater 35 is connected to the source 41 of power. The source 41 of power is connected to the control device 43 for controlling the supply of power from the source of power to the heater 33 and the valve 35, as well as to any other components of the aerosol generator.

The step of providing the pressurization arrangement 39 preferably includes positioning the source 37 of material in a chamber 47 and pressurizing the chamber, preferably to about two atmospheres. The source 37 of material preferably includes a flexible container 45. However, other embodiments are also possible. For example, as described with reference to FIGS. 5 and 6A–6B, the source 337 of material may include a second tube 345 having first and second ends 345a, 345b, the first end of the second tube being connected to the second end 31 of the tube 27 and the second end 345b of the second tube being positioned in the chamber 345.

In making the aerosol generator 21 according to the present invention, it is particularly preferred that the heater 33, the tube 27, the valve 35, the source 37 of material, and the pressurization arrangement 39 are arranged relative to each other to form a first component 23, and that the source 41 of power and the control device 43 are arranged relative to each other to form a second component 25, and that the second component is attachable to and detachable from the first component. In this way, the second component 25 can be made as a permanent device, with most or all of the more expensive features of the aerosol generator being associated with the second component, and the first component 23, which preferably includes the depletable or less expensive components of the aerosol generator, can be disposable. The different features of the aerosol generator 21 can be provided on whichever one of the components 23 and 25 seems appropriate for a particular application. However, according to the presently envisioned preferred application of the aerosol generator as a medical inhaler device, it is believed that the arrangement of features on the components 23 and 25 properly distributes the more and less disposable features.

The aerosol generator 21 is preferably used by a user providing a first signal, indicative of a user's intention to use the aerosol generator, to the control device 43. The first signal may be provided by the user pressing a button 58 (FIG. 2, in phantom) but, particularly where the aerosol generator 21 is intended to be used as an inhaler device, it is preferred that the first signal be provided by some form of draw-actuated device, such as a pressure drop detecting sensor 53 or, more preferably, an air flow detecting sensor 51.

The control device 43, in response to the first signal, sends a second signal to the source of power 41 to cause the source of power to open the openable and closeable valve 35. The valve 35 is preferably disposed between the tube 27 and the source 37 of material. Opening of the valve 35 permits material from the source 37 of material to flow from the source of material and into the tube 27.

Material from the source 37 of material is caused to flow from the source of material and into the tube 27, preferably by means of the pressurization arrangement. The source 37 of material preferably includes the flexible container 45, and material in container is caused to flow from the source of material by a pressurization arrangement 39. The pressurization arrangement 39 preferably includes the chamber 47 filled with gas G under pressure and in which the flexible container 45 is disposed. In an alternative embodiment, as described with reference to FIGS. 5 and 6A–6C, the source 337 of material includes the second tube 345 having first and second ends 345a, 345b. The first end 345a of the second tube 345 is connected to the second end 31 of the tube 27, and material in the source 337 of material is caused to flow from the source of material by the pressurization arrangement 339. The pressurization arrangement 339 includes a chamber 347 filled with gas G under pressure and in which the second end 345b of the second tube 345 is disposed.

A third signal is sent by the control device 43 and in response to the first signal to the source 41 of power to supply power to the heater 33 disposed relative to the tube 27 to heat the tube. Material from the source 37 of material is heated in the tube 27 with the heater 35 to a vaporization temperature such that the material volatilizes and expands out of the first end 29 of the tube.

The aerosol generator according to the present invention is preferably constructed in accordance with certain design principles that the inventors have recognized. These design relationships permit design of the aerosol generator with a certain robustness, particularly with respect to ambient temperature and container pressure variations, such that it is possible to ensure that the rate of aerosol delivery is substantially constant. While not wishing to be bound by theory, one relationship involves the rate at which aerosol is delivered (D), which is understood to be substantially linearly related to the pressure delivered to the liquid to be volatilized, i.e., the pressure (P), according to the relationship: $D=k_1 P$, where $k_1$ is substantially constant and depends upon design factors peculiar to the particular aerosol generator.

The control device 43 can be programmed to ensure that as the pressure of the gas G drops certain changes in operation to accommodate these changes will take place. For example, as the pressure of the gas G drops, delivery of the same amount of material will take a longer time. Accordingly, the control device 43 can be programmed to, for example, keep the valve 35 open for a longer time. While not wishing to be bound by theory, in the case where the flow passage comprises a circular bore of capillary tube, for a given aerosol delivery rate D, tube diameter d could be chosen taking into account the effect of tube diameter upon particle size.

It is desirable that an inhaler deliver an accurately repeatable volume of medication to a user. In developing an inhaler which operates by volatilizing a fluid delivered to a heated flow passage such as a tube, it is desirable to deliver a repeatable and precise volume to the heated tube. Thus, a metering device for use in an inhaler according to the invention is preferably capable of reliably delivering a known volume of fluid to an aerosolizing portion of an inhaler (e.g., a heated tube).

According to one embodiment of the invention, an inhaler is provided wherein one or more parts contacted by medicated fluid are disposable after a particular number of delivered inhalation doses (e.g., 200). As such, it would be desirable for a metering device of such an inhaler to have a simple and cost-efficient design including a minimum number of wetted parts.

A metering device in accordance with a preferred embodiment of the present invention includes a pressurized source of medicated fluid and a metering chamber which provides precise and repeatable volumetric dispensing of the fluid. The metering device preferably includes a small number of wetted parts and is simple to manufacture.

For a better understanding of the invention, the following detailed description refers to the accompanying drawings, wherein exemplary embodiments of the present invention are illustrated and described.

Figure 7:
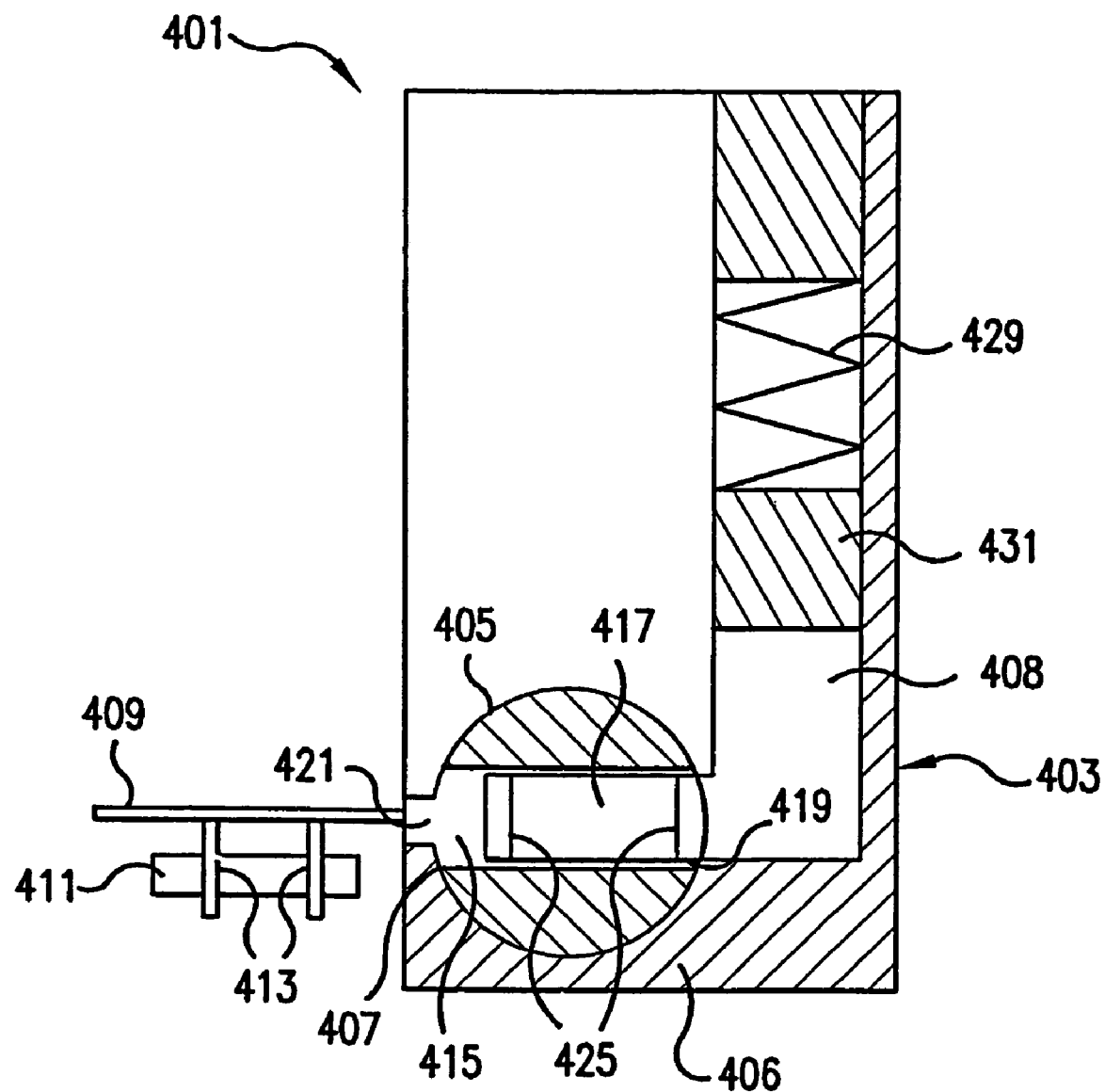
FIG. 7 is a schematic cut-away view of a metering device according to the present invention.

An inhaler 401 including an exemplary metering device 403 is shown schematically in FIG. 7. In this example, a rotary valve 405 in a housing 406 contains a metering chamber 407. The rotary valve 405 is located between a pressurized source of fluid 408 and a heated flow passage comprising a tube 409 in which the fluid is volatilized to produce an aerosol for inhalation by a user. The tube 409 can be heated by any suitable arrangement. For example, a power source 411 and electrical connections 413 for heating the tube 409 via a heater (not shown) are also shown schematically in FIG. 7.

In this example the metering chamber 407 in the rotary valve includes a bore 415 containing a sliding or "floating" piston 417. First and second openings 419, 421 at each end of the bore 415 can have diameters smaller than the diameter of the piston 417 so that the piston 417 is contained within the bore 415. However, the piston 417 can be maintained in the bore 415 by any suitable arrangement such as by providing suitably sized flow passages in housing 406 which contain the piston in the bore. A predetermined volume is defined as the difference between the volume of the bore 415 and the volume of the piston 417.

According to this arrangement the predetermined volume is delivered with each stroke of the piston 417. For example, pressurized fluid enters the first opening 419 in the rotary valve and moves the sliding piston 417 from a first position where the sliding piston 417 is adjacent the first opening 419 in the bore to a second position where the sliding piston 417 is adjacent to the second opening 421, thereby loading the predetermined volume of fluid into the rotary valve 405. When the rotary valve 405 is rotated to bring the second opening 421 of the bore into fluid communication with the pressurized source of fluid 408, the sliding piston 417 moves under pressure of the fluid from the first position to the second position to eject the predetermined volume out of the first opening 419 into a heated tube 409 and load a new predetermined volume through the second opening 421 in the rotary valve 405. Thus, in the example shown in FIG. 7, each 180° turn of the rotary valve 405 simultaneously ejects a predetermined volume of fluid and loads the next predetermined volume of the fluid. The rotary valve can be rotated by any suitable technique, e.g., manually such as by actuation of a push button connected to suitable gears or linkage or electronically such as by actuation of a switch which operates a motor connected to the valve. A push button actuator is discussed in more detail in connection with the dose metering device shown in FIGS. 9 and 10.

Preferably, to prevent fluid leakage, the piston 417 includes one or more sliding seals such as O-rings 425 which also separate a load side of the piston from an ejection side of the piston 417. Other means of sealing the load side of the piston 417 from the ejection side of the piston 417 are also within the scope of the invention. For example, the piston 417 can be designed in a manner and/or made of a material which provides one or more sections which matingly engage the bore to slidingly seal the ejection side of the load side.

The predetermined volume is determined by the difference between the volume of the sliding piston 417 and the volume of the bore 415. For example a 5 µl volume can be delivered by a piston having a 0.093 inch diameter and a stroke of 0.048 inches within the bore 415. The predetermined volume can be modified simply by changing a single dimension of the metering chamber 407. For example the predetermined volume can be increased by shortening the piston 417 or increasing the length of the bore 415, thereby increasing the stroke of the piston 417. Accordingly, the predetermined volume can be easily and inexpensively modified to accommodate children's inhalation doses and adult inhalation doses, as well as the varying delivered volumes required for a range of medications.

According to a modified embodiment, the piston can be replaced with a flexible diaphragm 427 secured within the bore 415. An example of a rotary valve of this sort is shown schematically in FIG. 8 wherein the volume in one side of the bore is ejected when the diaphragm 427 is displaced by fluid from the pressurized source of fluid 408 filling the other side of the bore. The predetermined volume is determined by the volume of the bore 415 on an ejection side of the diaphragm 427 displaced by the diaphragm 427. An advantage of the displacement member being a diaphragm is that there is less chance of the pressurized fluid bypassing the displacement member or of the displacement member malfunctioning as a result of incomplete movement along the bore.

Figure 8:
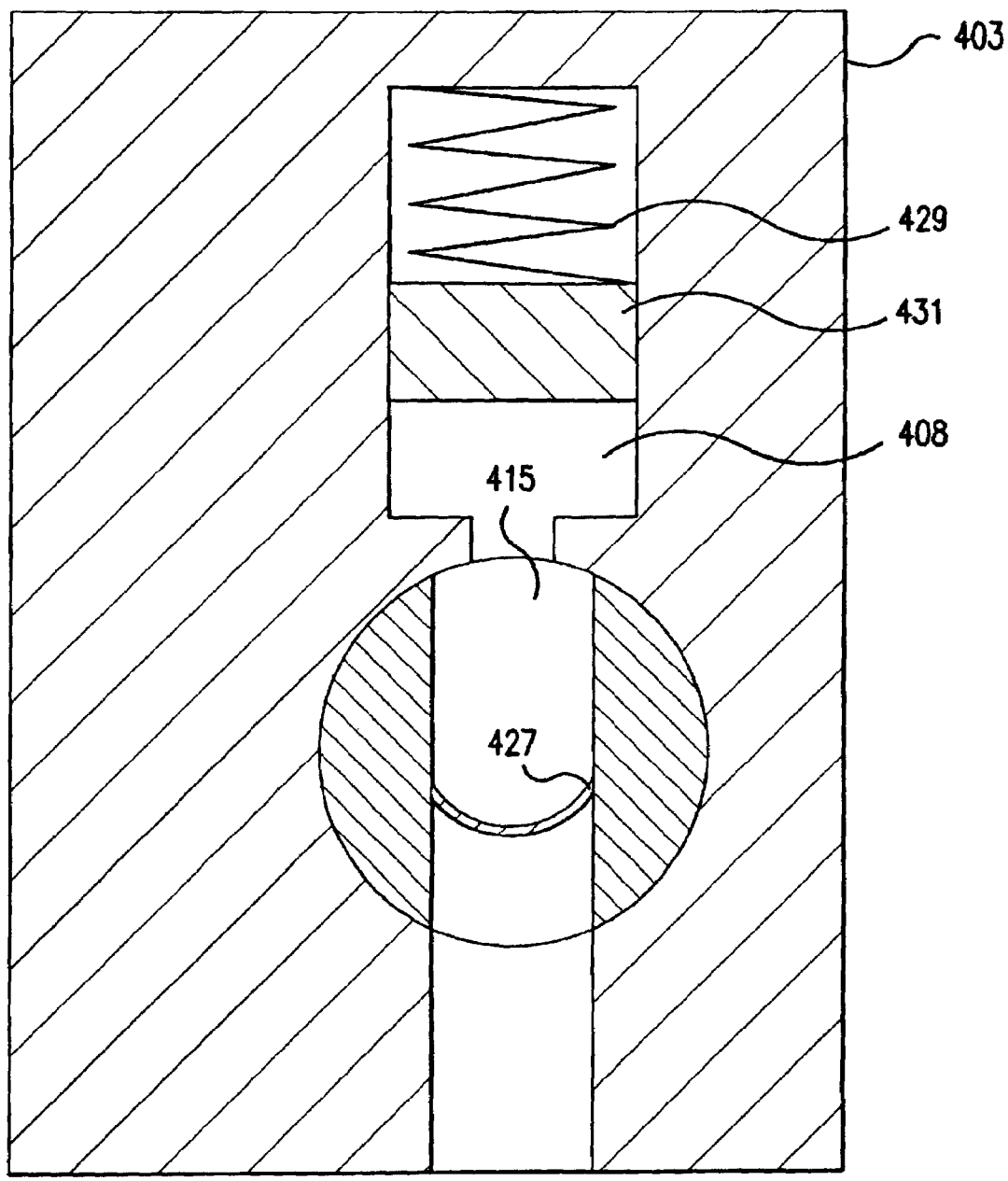
FIG. 8 is a schematic view of a metering device according to the present invention.

It is desirable that the pressurized source of fluid 408 maintain a substantially constant pressure as fluid is depleted from the pressurized source 408. That is, it is preferred that there be an insignificant change in pressure of the fluid delivered by the source 408 between delivery of the first delivered volume and the last delivered volume. The source of fluid 408 can be pressurized in any suitable manner. For instance, as shown in FIGS. 7 and 8, an elastic member such as a spring 429 can be used to bias a piston 431 against the fluid. Alternately, a pressurized gas can bias a piston against the fluid or fluid contained in a sealed collapsible bag. When a spring and piston mechanism is used to pressurize the source of fluid, the stroke of the piston is preferably small relative to the volume of fluid contained in the source to minimize the change in pressure as the fluid is depleted.

Figure 9:
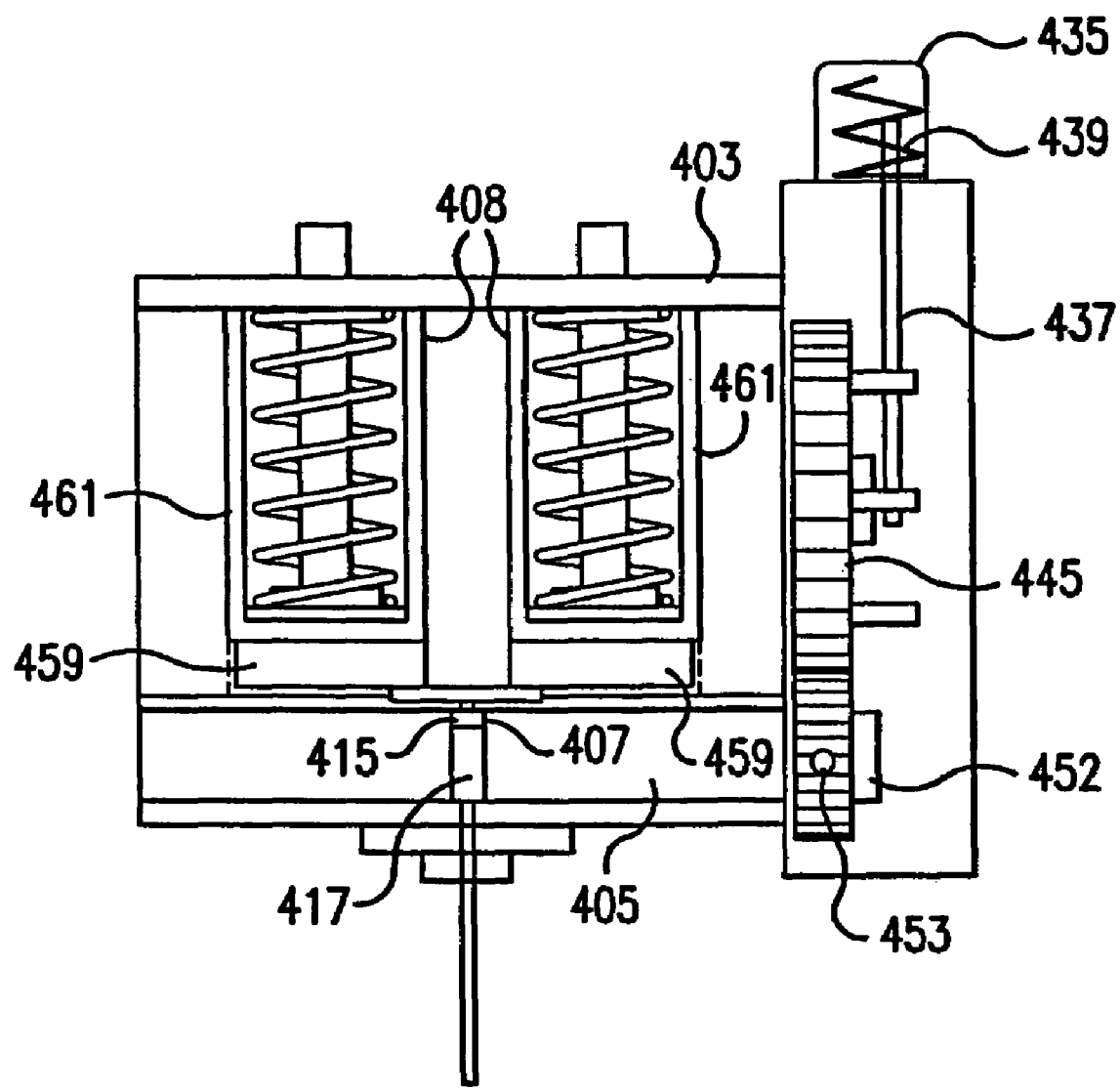
FIG. 9 is a front schematic cut-away view of the metering device shown in FIG. 7.
Figure 10:
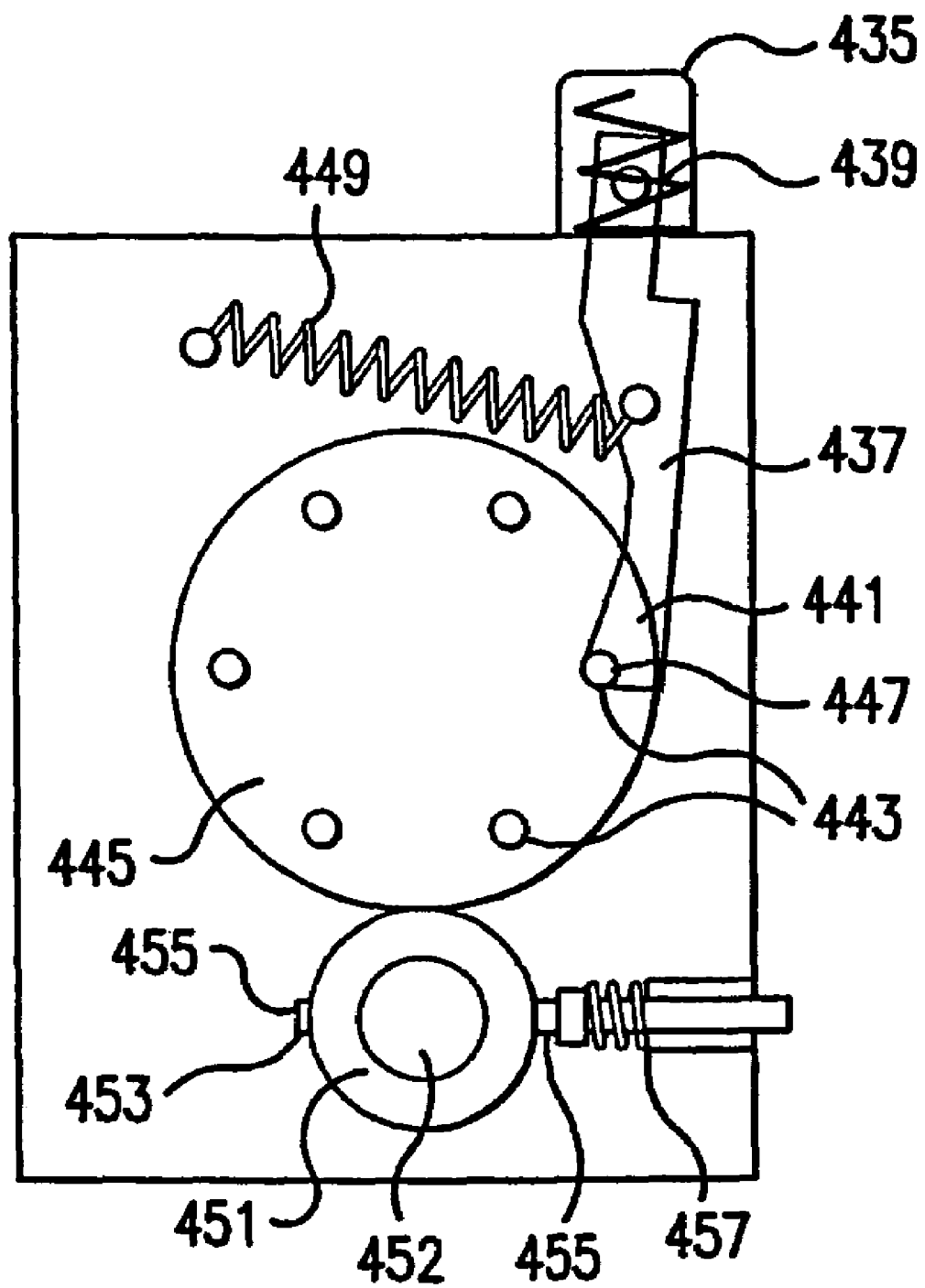
FIG. 10 is a side schematic cut-away view of the metering device shown in FIG. 8.
Figure 11B:
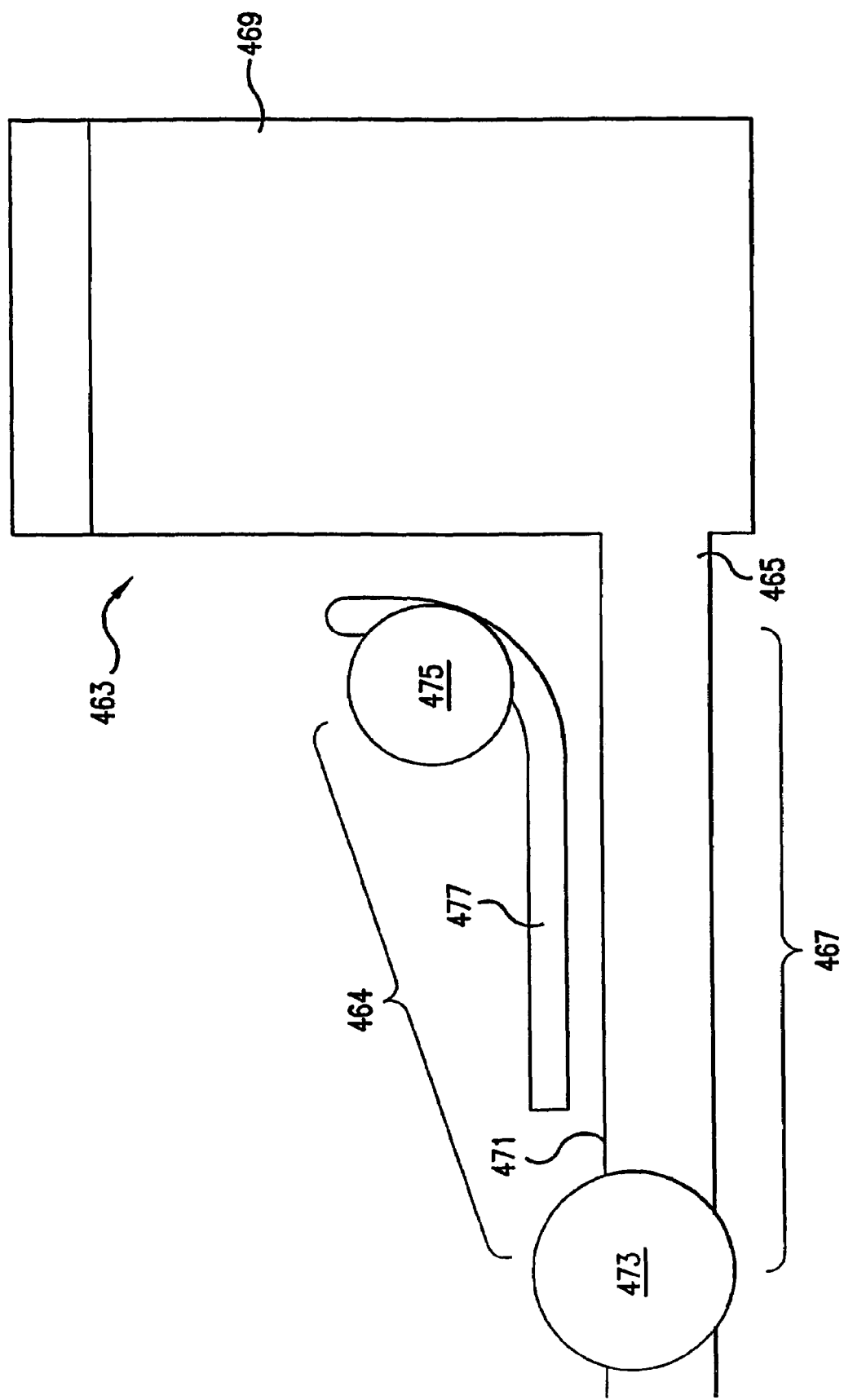
Figure 11C:
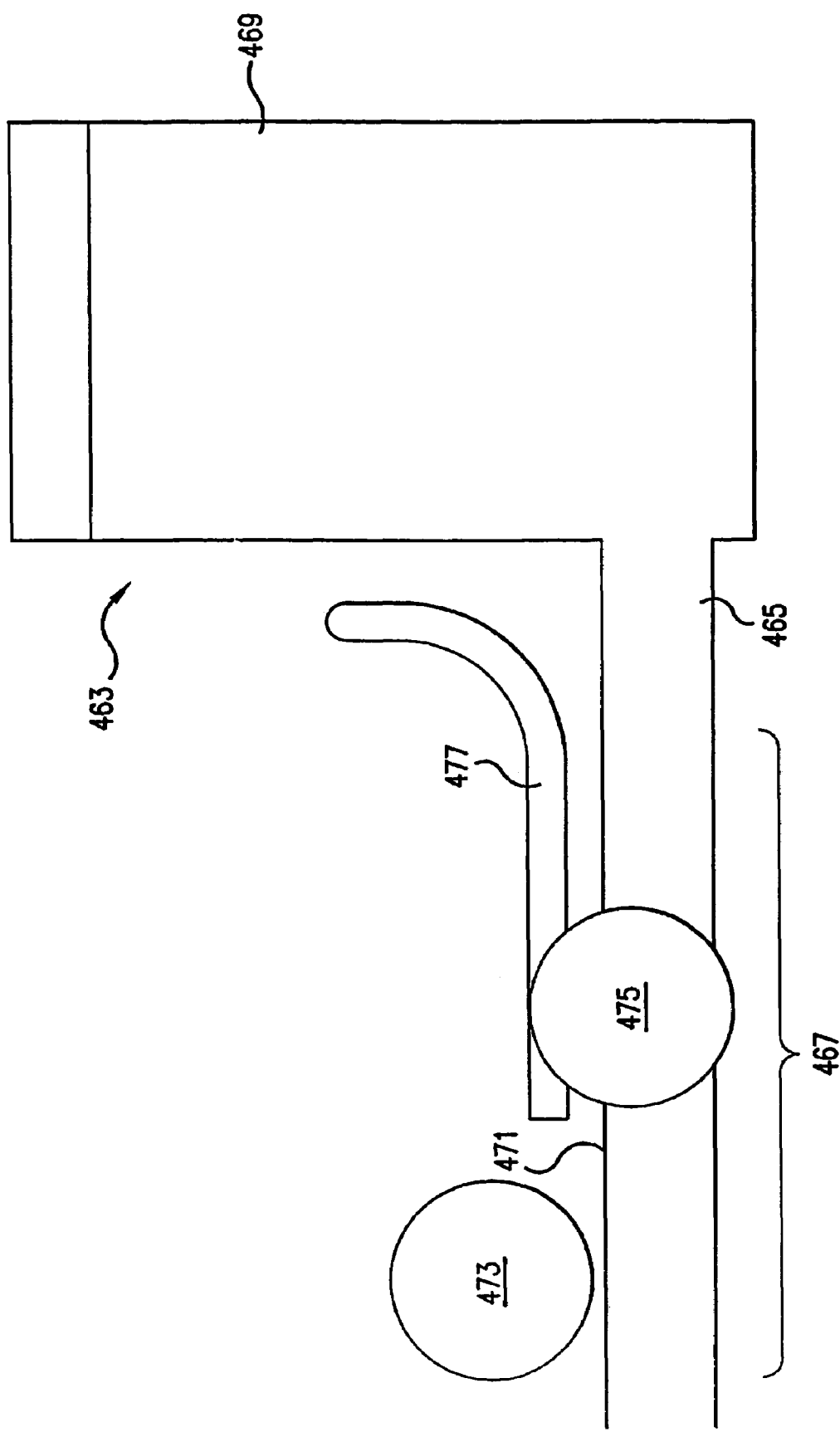

An example of a mechanism for actuating the rotary valve 405 is shown schematically in FIGS. 9 and 10 wherein the rotary valve 405 can be actuated by a spring-loaded pushbutton 435. Each time the spring-loaded pushbutton 435 is depressed, the rotary valve 405 is rotated approximately 180° thereby ejecting the predetermined volume of fluid out of the bore 415. The pushbutton mechanism includes a spring-loaded pushbutton 435 pivotable connected to a ratchet arm 437. A proximal end 439 of the ratchet arm 437 is pivotably attached to the pushbutton 435 and the distal end 441 of the ratchet arm 437 engages a pin 443 on a first gear 445 with a notch 447 at the distal end 441 of the ratchet arm 437. The first gear includes six pins 443 spaced 60° apart. As the button 435 is depressed, the ratchet arm 437 exerts force on one of the six pins 443 pushing the first gear 445 in a clockwise direction. A spring 449 is attached at one end to a part of the inhaler which is stationary with respect to the movement of the ratchet arm 437. Another end of the spring 449 is attached to the ratchet arm 437 and pulls the ratchet arm 437 back to a start position after the button 435 has been depressed. The notch 447 at the distal end 441 of the ratchet arm 437 is then positioned adjacent a next pin of the first gear 445.

The first gear 445 engages a second gear 451 which is on a shaft 452 connected to the rotary valve 405. As the shaft 452 is rotated, the bore 415 is rotated relative to the source of fluid 408. For example, the first gear 445 can include 60 teeth and the second gear 451 can include 20 teeth such that when the first gear is rotated 60° the second gear 451 rotates 180°.

It is desirable to time heating of the flow passage in a capillary aerosol type inhaler with the ejection of the predetermined volume of fluid so that the fluid is efficiently volatilized in the flow passage. An exemplary timing device includes a pair of contacts or cam surfaces 453 on the second gear 451 to provide exposed ends 455 spaced about 180° from one another. A spring-loaded electrical contact or switch 457 is connected to a heating mechanism (not shown) for the flow passage. The spring loaded electrical contact or switch 457 is triggered each time it makes contact with an end of the surface 457. Thus, according to this embodiment, each 180° rotation of the shaft 452 containing the rotary valve 405 ejects a predetermined volume, loads a predetermined volume and triggers the heating mechanism to heat the attached flow passage.

As mentioned in the embodiment described in FIG. 7, it is desirable to maintain a constant pressure in the pressurized source of fluid. An example of a mechanism minimizing the pressure loss as the fluid source is depleted is shown in FIG. 9. In this example, the metering chamber 407 is in fluid communication with a source 408 including two reservoirs 459 of pressurized fluid. Each reservoir 459 has a spring-loaded piston 461 which travels a shorter distance over the dispensing of the entire source volume than a single spring and piston arrangement having the same cross-sectional area as one of the two piston and reservoir arrangements. In this way, the difference in pressure exerted against the fluid in the initial filled condition and a later depleted condition can be minimized.

Another example of a metering device 463 according to the present invention is shown schematically in FIGS. 11–13. In this example, a metering chamber 464 is part of a delivery passage 465 having an elastic portion 467. A source of medicated fluid 469 is in fluid communication with the delivery passage 465. The elastic portion 467 of the delivery passage 465 is deformed to eject a predetermined volume of fluid out of the delivery passage 469.

FIGS. 11A–11C schematically show an embodiment of a metering device 463 according to the present invention. In this example, the delivery passage 465 is formed out of an elastic tube 471. The elastic tube 471 can be formed of silicone or other known elastic materials. A first deforming member such as a pinch roller 473 deforms the elastic tube 471 such that fluid is prevented from flowing through the tube downstream of the roller 473. Upstream of the first deforming member 473 is a second deforming member such as a metering roller 475. The metering roller 475 is configured to travel a predetermined path 477. In at least a portion of the path 477, the metering roller 475 acts as a displacement member when it comes into contact with the elastic tube 471 to deform a portion of the elastic tube 471 and exert pressure on the fluid contained therein. Simultaneously, the pinch roller 473 is moved sufficiently to allow predetermined volume of fluid to be ejected from the tube 471. The pinch roller 473 may be withdrawn or raised by the pressure generated by the metering roller 475 or by a suitable mechanical arrangement like the arrangements shown in FIGS. 12 and 13.

The predetermined volume is determined by an inner diameter of the elastic tube 471 and the length of the tube 471 which is sealed off and emptied by the metering roller 475. As in the other examples illustrating the present invention, the predetermined volume can be varied by changing a single dimension of the metering device. For example, to increase the predetermined volume, an inner diameter of the elastic tube 471 or path of roller 475 can be increased.

An advantage of this example of a metering device 463 is that the fluid can be isolated in the elastic tube thus avoiding direct contact with moving parts. Also, in a reusable inhaler, the liquid source can be designed to be replaced with a cartridge having the delivery passage 465 attached thereto after a predescribed number of metered volumes have been delivered by a depleted liquid source.

Another example of a metering device 463 according to present invention is shown schematically in FIGS. 12 and 13. In this example, the source of fluid 469 is pressurized by a spring 479 connected to a piston 481. A metering chamber 483 is part of a delivery passage 485 which includes an elastic portion 487. The elastic portion 487 of the delivery passage 485 is formed by an elastic sheet 489 (FIG. 13) sealed over a portion of the delivery passage 485. The elastic sheet 489 can be formed of silicone or other suitable elastic material.

In the example shown, a wheel 491 including five rollers 493 is located adjacent the elastic portion 487 of the delivery passage 485. Each roller 493 is separated from adjacent rollers by 72°. The wheel 491 is arranged adjacent the elastic portion 487 of the delivery passage 485 so that as the wheel 491 is rotated the convex surfaces of the rollers 493 deform the elastic sheet 489 into and against the convex surface of the delivery passage 485.

Figure 12:
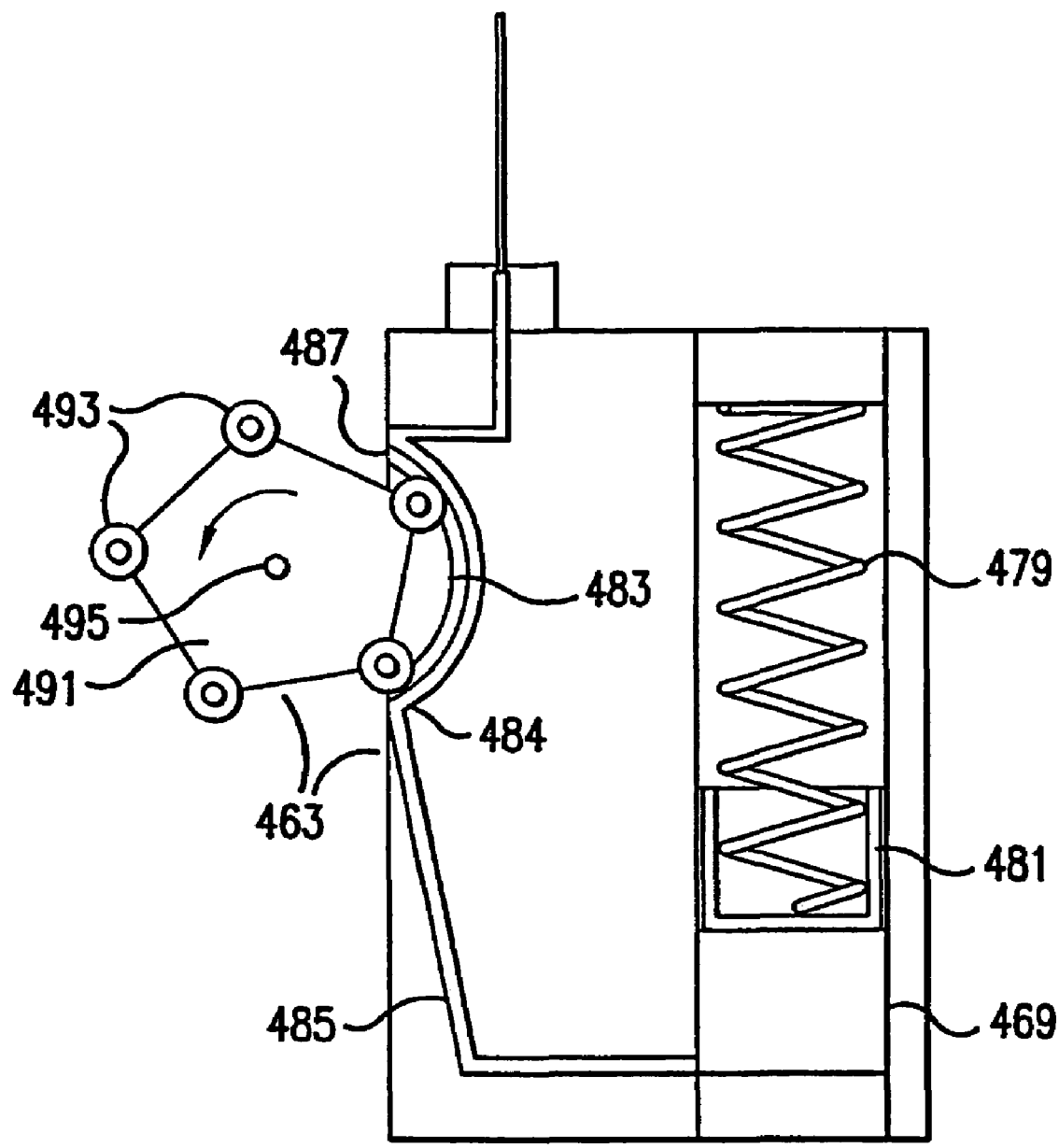
FIG. 12 is a front schematic cut-away view of a modified metering device according to the present invention.
Figure 13:
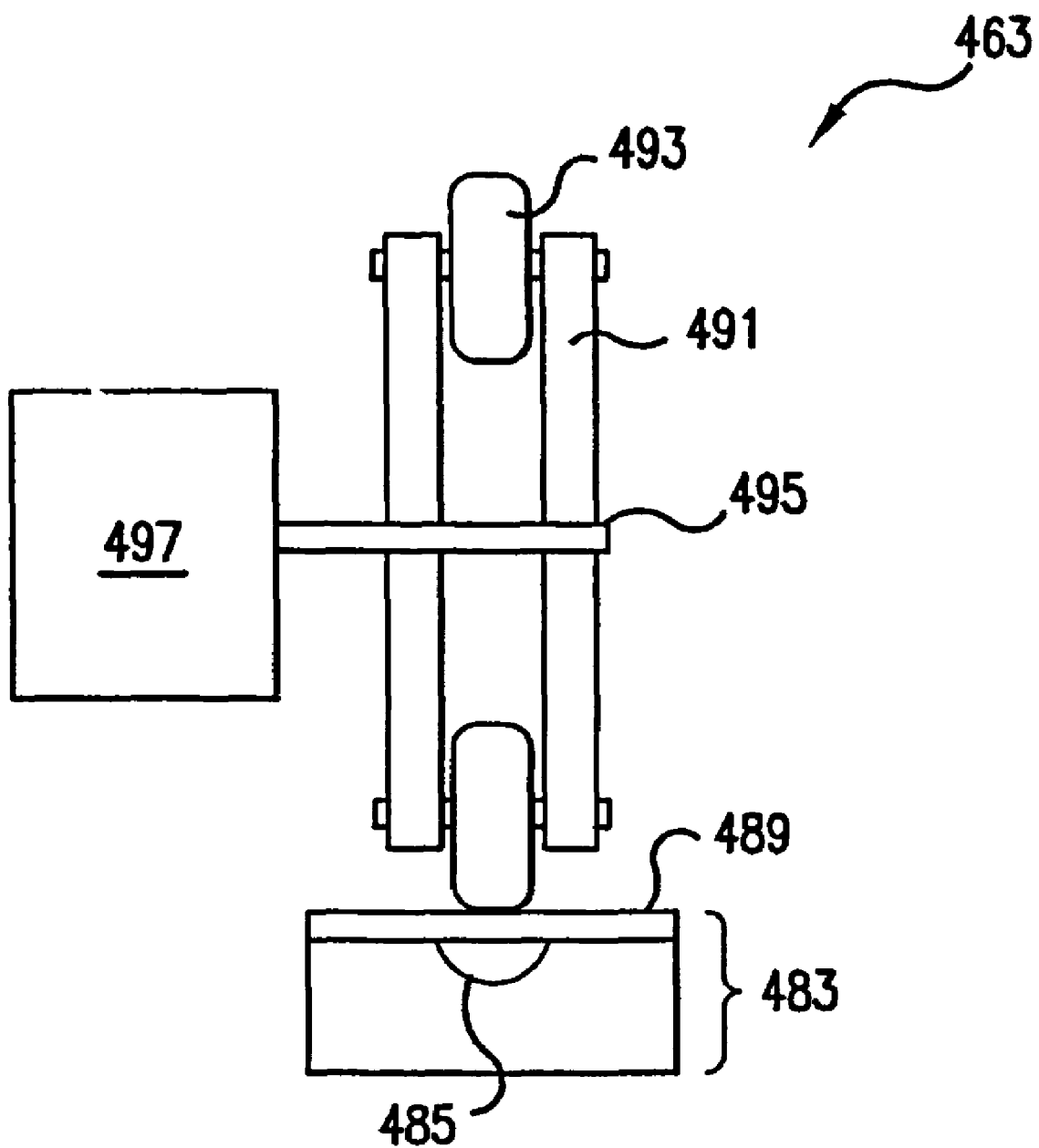
FIG. 13 is a side schematic cut-away view of a portion of the delivery passage shown in FIG. 12.

As shown in FIGS. 12 and 13, the portion of the delivery passage between the rollers 493 in contact with the sheet 489 defines a metered volume of liquid to be delivered to the inhaler. As the wheel 491 rotates 72°, the rollers 493 in contact with the elastic sheet 489 move the fluid contained in the delivery passage 485 between the rollers in a downstream direction for delivery to a spray mechanism of the inhaler. The pressurized source of fluid 469 fills the passage 485 as the rollers 493 pass inlet 484 of the metering chamber 483. In this way, a predetermined volume of the fluid can be urged through the delivery passage into a heated flow passage of an inhaler which ejects the volatilized fluid to form an aerosol spray. The volume of the delivery channel contained between two adjacent rollers determines the predetermined volume and is dependent on the distance between the adjacent rollers 493 on the wheel 491. In the embodiment shown in FIGS. 12 and 13, a metered volume is ejected each time the wheel 491 is rotated 72°.

The wheel 491 rotates on a shaft 495 which can be turned manually or with a mechanical, or electromechanical mechanism. For example, the shaft 495 can be turned by a conventional spring driven clock motor 497. According to this arrangement the flow rate of fluid ejected can be controlled in addition to the predetermined volume. The clock motor 497 controls the time period and rate at which the wheel 491 rotates the predetermined distance. In this way, the predetermined volume can be metered at a predetermined rate.

The components of the metering chamber according to the present invention can be manufactured using conventional injection molding techniques. The components can be molded out of plastic resins or other materials known to be appropriate for inhaler applications.

According to the present invention a metering device can be provided which delivers a repeatable, precise volume of a medicated fluid in an inhaler. In addition, the metering device according to the present invention has few wetted parts and is simple to manufacture. Accordingly, the metering device according to the present invention is well suited for use in inhalers and in particular heated capillary aerosol inhalers.

While this invention has been illustrated and described in accordance with a preferred embodiment, it is recognized that variations and changes may be made therein without departing from the invention as set forth in the claims. For instance, the aerosol generator could include arrangements for manually operating the valve 35, i.e., instead of actuation by detection of air flow or pressure drop, with the controller 43 being configured to execute a scheduled heating cycle upon receipt of a signal indicating actuation of the valve. Such arrangements might further include devices (electrical or mechanical) to maintain the valve 35 in an opened position for a predetermined amount of time once it is mechanically actuated. Further, the mouthpiece is optional and need not be incorporated in inhalers or other devices utilizing the aerosol generator according to the invention.

The invention claimed is:

1. A hand-held inhaler, comprising:
   a mouthpiece:
   a heater;
   a medicament containing material to be volatilized;
   a source of power operating the heater; and
   a programmed control device controlling a supply of power from the source of power to the heater;
   a pressure drop detecting device which determines when a predetermined pressure drop occurs in the mouthpiece, the pressure drop detecting device being arranged to send a signal to the control device to indicate that the predetermined pressure drop is occurring, and the control device being arranged to control the power source to supply power to the heater in response to the signal from the pressure drop detecting device,
   the material being located in a first component of the inhaler and the control device and the source of power being located in a second component of the inhaler, the first component being a disposable component removably attached to the second component and the heater being operable to volatilize the material and form an aerosol in the mouthpiece of the inhaler.

2. The inhaler as set forth in claim 1, further comprising an air flow detecting device arranged to send a signal to the control device to indicate that a predetermined air flow rate exists in the mouthpiece, and the control device being arranged to control the power source to supply power to the heater in response to the signal from the air flow detecting device, the mouthpiece having a plurality of vent holes through which ambient air enters the mouthpiece.

3. The inhaler as set forth in claim 1, wherein the control device includes a timer for controlling a frequency with which the control device controls the power supply to supply power to the heater, the inhaler optionally including a remote control device adapted to adjust the timer to adjust the frequency with which the control device controls the power supply to supply power to the heater wherein the timer optionally includes an indicator for indicating that the control device is available to control the power supply to supply power to the heater.

4. The inhaler as set forth in claim 1, further comprising a display device controlled by the control device and displaying a number of times that the control device controls the power supply to supply power to the heater, the control device optionally including a timer for controlling a frequency with which the control device controls the power supply to supply power to the heater, the inhaler optionally including a remote control device adapted to adjust the timer to adjust the frequency with which the control device controls the power supply to supply power to the heater, and the display optionally indicating when the timer will permit the control device to control the power supply to supply power to the heater.

5. The inhaler as set forth in claim 1, wherein a rate of power supplied from the source of power to the heater produces an aerosol having a mass median particle diameter of less than 3 microns, preferably less than 2 microns, more preferably between 0.2 and 2 microns and most preferably between 0.5 and 1 microns.

6. The inhaler as set forth in claim 1, wherein the material is a liquid material in fluid communication with a flow passage heated by the heater.

7. A method of generating an aerosol using a hand-held inhaler having a disposable first component removably attached to a reusable second component, comprising:

generating a first signal, indicative of a user's intention to generate an aerosol, to a programmed control device in the second component;

sending responsively to the first signal, a second signal to a source of power in the second component, the source of power being operable to supply power to a heater arranged to heat a medicament containing material to be volatilized in the first component;

forming an aerosol of the volatilized material in a mouthpiece of the inhaler such that the aerosol can be inhaled by the user drawing on an outlet in the mouthpiece; and replacing a first component with another first component.

8. The method as set forth in claim 7, wherein the first signal is provided by a user pressing a button or the first signal is provided by a user drawing on the mouthpiece in such a manner as to operate an air flow detecting device.

9. The method as set forth in claim 7, wherein the material to be volatilized is a liquid material.

10. The method as set forth in claim 7, wherein the material to be volatilized is heated in a flow passage which vaporizes a predetermined volume of the material so as to form an aerosol spray.

11. The method as set forth in claim 7, wherein the aerosol has a mass median particle diameter of less than 3 microns, preferably less than 2 microns, more preferably between 0.2 and 2 microns and most preferably between 0.5 and 1 microns.

* * * * *